(12) United States Patent
Sharma et al.

(10) Patent No.: US 11,236,045 B2
(45) Date of Patent: Feb. 1, 2022

(54) SUBSTITUTED SULFOXIMINE COMPOUNDS

(71) Applicant: CADILA HEALTHCARE LIMITED, Gujarat (IN)

(72) Inventors: Rajiv Sharma, Ahmedabad (IN); Pravin Iyer, Ahmedabad (IN); Sameer Agarwal, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 16/617,389

(22) PCT Filed: Jun. 8, 2018

(86) PCT No.: PCT/IB2018/054134
§ 371 (c)(1),
(2) Date: Nov. 26, 2019

(87) PCT Pub. No.: WO2018/225018
PCT Pub. Date: Dec. 13, 2018

(65) Prior Publication Data
US 2020/0140382 A1    May 7, 2020

(30) Foreign Application Priority Data
Jun. 9, 2017  (IN) .............................. 201721020305

(51) Int. Cl.
| | | |
|---|---|---|
| *C07C 381/10* | (2006.01) | |
| *C07D 213/71* | (2006.01) | |
| *C07D 213/76* | (2006.01) | |
| *C07D 215/36* | (2006.01) | |
| *C07D 231/38* | (2006.01) | |
| *C07D 265/30* | (2006.01) | |
| *C07D 305/08* | (2006.01) | |
| *C07D 307/64* | (2006.01) | |
| *C07D 319/16* | (2006.01) | |
| *C07D 333/34* | (2006.01) | |
| *A61P 29/00* | (2006.01) | |
| *A61K 31/4406* | (2006.01) | |

(52) U.S. Cl.
CPC ........ *C07C 381/10* (2013.01); *A61K 31/4406* (2013.01); *A61P 29/00* (2018.01); *C07D 213/71* (2013.01); *C07D 213/76* (2013.01); *C07D 215/36* (2013.01); *C07D 231/38* (2013.01); *C07D 265/30* (2013.01); *C07D 305/08* (2013.01); *C07D 307/64* (2013.01); *C07D 319/16* (2013.01); *C07D 333/34* (2013.01)

(58) Field of Classification Search
CPC . C07C 381/10; C07C 2603/10; C07D 213/71; C07D 213/76; C07D 215/36; C07D 231/38; C07D 265/30; C07D 305/08; C07D 307/64; C07D 319/16; C07D 333/34; C07D 319/18; C07D 295/096; C07D 213/70; A61P 29/00; A61K 31/4406
See application file for complete search history.

(56) References Cited

U.S. PATENT DOCUMENTS

| | | | |
|---|---|---|---|
| 4,666,506 A | | 5/1987 | Hillemann |
| 5,258,406 A | * | 11/1993 | Toth ..................... C07C 381/10 |
| | | | 514/593 |
| 2002/0077486 A1 | | 6/2002 | Scarborough et al. |

FOREIGN PATENT DOCUMENTS

| | | |
|---|---|---|
| WO | 1998032733 A1 | 7/1998 |
| WO | 20160131098 A1 | 8/2016 |
| WO | 2019023147 | 1/2019 |
| WO | 2019068772 | 4/2019 |

OTHER PUBLICATIONS

Toth J. E. et al, Sulfonimidamide Analogs of Oncolytic Sulfonylureas, Journal of Medicinal Chemistry, 1997, pp. 1018-1025, vol. 40, No. 6.
Database PubChem Compound [Online], XP002783838, retrieved from NCBI Database accession No. 10787134 compound 10787134, Oct. 26, 2006.
Database Registry [Online] Chemical Abstracts Service, Columbus, Ohio, US; Jun. 13, 2008, XP002783839, retrieved from STN Database accession No. 1027831-60-2 compounds 1027831-60-2.
European Patent Office, Munich, International Preliminary Report on Patentability, dated Jul. 25, 2019, PCT/IB2018/054134.
European Patent Office, Third Party Observation for application No. EP20180739634, Filed Sep. 8, 2021, Transmitted to Applicant on Sep. 20, 2021, Munich, Germany.

* cited by examiner

*Primary Examiner* — Amanda L. Aguirre
(74) *Attorney, Agent, or Firm* — IpHorgan Ltd.

(57) ABSTRACT

The present invention relates to novel heterocyclic compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions as well as treatment of disease states mediated by NLRP3 as well as treatment of diseases or conditions in which interleukin 1β activity and interleukin-18 (IL-18) is implicated.

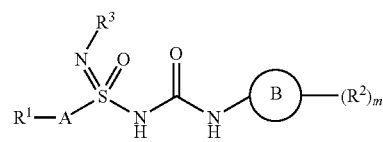

Formula (I)

7 Claims, No Drawings

SUBSTITUTED SULFOXIMINE COMPOUNDS

CROSS REFERENCE TO RELATED APPLICATIONS

This application is a national stage completion application of PCT Application No. PCT/IB2018/054134, filed Jun. 8, 2018, and claims priority from India Application No. 201721020305, filed Jun. 9, 2017.

FIELD OF THE INVENTION

The present invention relates to novel heterocyclic compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions as well as treatment of disease states mediated by NLRP3 as well as treatment of diseases or conditions in which interleukin 1β activity and interleukin-18 (IL-18) is implicated.

BACKGROUND OF THE INVENTION

The NOD-like receptor family (NLR) protein NLRP3 is an intracellular signaling molecule that senses many pathogens, environmental and host-derived factors. (Wen., et. al., Immunity. 2013; 39:432-441). Activation of NLRP3 leads to binding with apoptosis associated speck-like protein containing a CARD (ASC). ASC in turn interacts with the cysteine protease caspase-1, forming a complex termed the inflammasome. This results in the activation of caspase-1, which cleaves the pro-inflammatory cytokines IL-1β and IL-18 to their active forms and mediates a type of inflammatory cell death known as pyroptosis. Other intracellular pattern recognition receptors (PRRs) are also capable of forming inflammasomes. These include other NLR family members such as NLRP1 and NLRC4 and non-NLR PRRs such as the double-stranded DNA (dsDNA) sensors absent in melanoma 2 (AIM2) and interferon, gamma inducible protein 16 (IFI16). (Latz, et. al., Nat Rev Immunol. 2013; 13:397-411) NLRP3-dependent IL-1β processing can also be activated by an indirect, non-canonical pathway downstream of caspase-1 (Lamkanfi, et. al., Cell. 2014; 157:1013-1022).

Inflammasome components such as NLRP3, ASC and caspase-1 are expressed in immune cells in the liver including Kupffer cells, infiltrating macrophages, hepatocytes, and hepatic stellate cells. Inflammasome activation is dependent on two successive signals. Signal 1 is driven by TLR and IL-1R signaling, includes expression of component proteins including NLRP3, ASC, pro-caspase-1, pro-IL-1β, and pro-IL-18. Signal 2 is provided by danger signals (DAMPS) that during NASH development are mainly released by stressed or dying hepatocytes or via a "leaky" gut (PAMPs). This process leads to oligomerization of the inflammasome components and cleavage of pro-caspase-1, leading to the release of active pro-inflammatory cytokines.

The NLRP3 inflammasome acts as a key mediator of inflammatory responses through the activation of caspase-1 leading to processing and release of the pro-inflammatory cytokines interleukin-1β (IL-1β) and interleukin-18 (IL-18). The NLRP3 inflammasome is a component of the inflammatory process and its aberrant activation is pathogenic in inherited disorders such as the rare periodic fever syndrome, cryopyrin associated periodic syndromes (CAPS), Tumor necrosis factor receptor-associated periodic syndrome (TRAPS) and complex diseases such as multiple sclerosis, type 2 diabetes, atherosclerosis, asthma, gouty arthritis, and inflammatory central nervous system (CNS) diseases. (Masters, et. al., Annu Rev Immunol. 2009; 27:621-668; Strowig, et. al., Nature 2012, 481, 278-286; Guo, et. al., Nat. Med. 2015, 21, 677.)

Inflammation is an essential host response to infection and injury. The regulation of the pro-inflammatory cytokine interleukin-1β (IL-1β), which is central to host responses to infection, also causes tissue injury when activated inappropriately. (Dinarello, et. al., Nat. Rev. Drug Discovery 2012, 11, 633-652.) NLRP3 inflammasome activation plays a key role in each of the components including induction of pro-inflammatory signaling, hepatocellular injury and cell death, and activation of the hepatic stellate cells (HSC) that are responsible for collagen deposition and liver fibrosis. In particular, the transition from NAFLD to NASH associates with NLRP3-inflammasome activation and an increased expression of inflammasome-related components, including apoptosis-associated speck-like protein containing a carboxy-terminal CARD (ASC), caspase-1 (CASP-1) and pannexin. (Mridha, et. al., Journal of Hepatology, 2017, 66 (5), 1037-1046)

Current treatments for NLRP3 related diseases include biologic agents that target IL-1. These are the recombinant IL-1 receptor antagonist Anakinra, the neutralizing IL-1β antibody Canakinumab and the soluble decoy IL-1 receptor Rilonacept.

Published patent applications WO98/32733, WO2001/019390, WO2014/190015, WO2016/123229 disclose certain WO/2016/131098 filed by The University Of Queensland disclosed sulfonylureas derivatives and related compounds as NLRP3 inflammasome inhibitors. WO2017/017469 filed by The University of Manchester, disclosed certain cyclic diarylboron derivatives as NLRP3 inflammasome inhibitors for the treatment of diseases or conditions in which interleukin 1 β activity is implicated. Some of the recent patent applications such as WO2017031161, WO2017079352 disclosed certain class of compounds as NLRP3 inhibitors.

We herein disclose novel heterocyclic compounds of general formula (I) which are NLRP3 Modulators for the prevention and treatment of disease states mediated by NLRP3 or conditions in which interleukin 1β activity and interleukin-18 (IL-18) are implicated, including inflammation, Cryopyrin-associated periodic syndromes (CAPS), gouty arthritis, type 2 diabetes, atherosclerosis, and liver fibrosis. More particularly, embodiments of the present invention are useful as therapeutics in the treatment of a variety of pathological conditions including (but not limited to) lymphoma, auto-immune diseases, heteroimmune diseases, inflammatory diseases, cancer, and neurodegenerative diseases or conditions.

SUMMARY OF THE INVENTION

The present invention discloses heterocyclic compounds as defined by the general formula (I) that are NLRP3 modulators for the prevention and treatment of disease states mediated by NLRP3 as well as treatment of diseases or conditions in which interleukin 1β activity and interleukin-18 (IL-18) are implicated. The compounds of the present invention are useful in the treatment of human or animal body, by inhibition of NLRP3. The compounds of this invention are therefore suitable for the prevention and treatment of disease states mediated by NLRP3.

EMBODIMENT(S) OF THE INVENTION

An embodiment of the present invention provides novel heterocyclic compounds represented by the general formula (I), their tautomeric forms, their enantiomers, their diastereoisomers, their stereoisomers, their pharmaceutically acceptable salts and pharmaceutical compositions containing them or their mixtures thereof.

In a further embodiment of the present invention is provided pharmaceutical compositions containing compounds of the general formula (I), their tautomeric forms, their enantiomers, their diastereoisomers, their stereoisomers, their pharmaceutically acceptable salts, or their mixtures in combination with suitable carriers, solvents, diluents and other media normally employed in preparing such compositions.

In a still further embodiment is provided the use of heterocyclic compounds of the present invention as NLRP3 modulators, by administering a therapeutically effective and non-toxic amount of compounds of general formula (I) or their pharmaceutically acceptable compositions to the mammals.

In a still further embodiment is provided a process for preparing the novel compounds of the present invention.

DESCRIPTION OF THE INVENTION

Accordingly, the present invention relates to the compounds of the general formula (I)

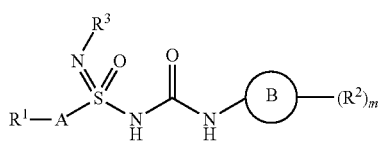

Formula (I)

their tautomeric forms, their stereoisomers, their pharmaceutically acceptable salts, and pharmaceutical compositions containing them wherein
'A' is selected from unsubstituted or substituted ($C_1$-$C_6$) alkyl, ($C_2$-$C_6$)alkenyl, ($C_3$-$C_6$)cycloalkyl, aryl, heteroaryl and heterocyclyl groups having optionally one or more than one heteroatoms;
$R^1$ at each occurrence independently represents hydrogen, halogen, haloalkyl, cyano, optionally substituted groups selected from ($C_1$-$C_6$)alkyl, ($C_2$-$C_6$)alkenyl, ($C_1$-$C_6$)alkoxy, ($C_3$-$C_6$)cycloalkyl, aryl, heteroaryl, heterocyclyl, benzyl, mercapto alkyl, sulfur and its oxidized form.
In an embodiment when A represents ring, $R^1$ may represent one or more substituents selected from hydrogen, halogen, haloalkyl, cyano, optionally substituted groups selected from ($C_1$-$C_6$)alkyl, ($C_2$-$C_6$)alkenyl, ($C_1$-$C_6$)alkoxy, ($C_3$-$C_6$)cycloalkyl, aryl, heteroaryl, heterocyclyl, benzyl, thiol, mercapto alkyl, sulfur and its oxidized forms, $C_1$-$C_6$ (thio-alkoxy), bridged or spiro ring system having optionally one or more than one heteroatoms;

'B' is selected from optionally substituted ($C_3$-$C_6$)cycloalkyl, aryl, heteroaryl and heterocyclyl or the following ring system

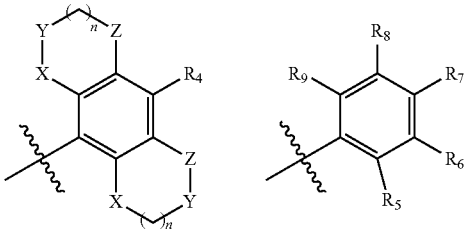

wherein X, Y, Z at each occurrence is independently selected from C, N, S, $SO_2$, and O, which may be, wherever possible be optionally substituted;
n=0-3
$R^2$ at each occurrence independently represents hydrogen, halide, cyano, optionally substituted groups selected from ($C_1$-$C_6$)alkyl, ($C_2$-$C_6$) alkenyl, ($C_1$-$C_6$)alkoxy ($C_3$-$C_6$)cycloalkyl, benzyl, aryl, heteroaryl, heterocyclyl, thiol, thioalkyl, thio-alkoxy sulfur and its oxidized forms, bridged or spiro ring system having optionally one or more than one heteroatoms;
$R^3$ at each occurrence independently represents hydroxyl, halogen, nitro, cyano, optionally substituted groups selected from ($C_1$-$C_{10}$)alkyl, ($C_1$-$C_{10}$)alkoxy, ($C_3$-$C_{10}$)cycloalkyl, ($C_2$-$C_{10}$) alkenyl, ($C_2$-$C_{10}$)alkynyl, $SO_2$($C_1$-$C_6$)alkyl, benzyl, aryl, heteroaryl, heterocyclyl, thiol, thioalkyl, thioalkoxy, (sulfur and its oxidized forms); in an embodiment, $R^3$ and A together with the atom to which they are attached may form a optionally substituted 5 to 7 membered heterocyclic ring system having optionally one or more than one heteroatoms; 'm' represents an integer from 1-5;
Each of $R_4$, $R_5$, $R_6$, $R_7$, $R_8$, and $R_9$ at each occurrence are independently selected from hydrogen, halogen, cyano, amide, sulphonamide, acyl, hydroxyl, optionally substituted groups selected from ($C_1$-$C_6$)alkyl, ($C_1$-$C_6$)haloalkyl, ($C_3$-$C_6$)cycloalkyl, ($C_1$-$C_6$)alkoxy; Alternatively each of $R_5$ and $R_6$, $R_7$ and $R_8$ or $R_8$ and $R_9$ wherever possible, together may form a 4 to 7 membered saturated or partially saturated ring containing from 0-2 additional heteroatoms selected from the group consisting of N, O, and $S(O)_p$; p=1-2.
When any of above defined group is substituted the substitutions on them may be selected from hydrogen, hydroxy, cyano, halo, haloalkyl, haloalkyloxy, alkylthio ($C_1$-$C_6$)alkyl, ($C_2$-$C_6$)alkenyl, ($C_2$-$C_6$)alkynyl, ($C_3$-$C_{10}$)cycloalkyl, $C_1$-$C_6$ alkoxy, —$COR_{10}$, —$CSR_{10}$, $C(O)OR_{10}$, $C(O)$—$R_{10}$, —$C(O)$—$NR_{11}R_{12}$, —$C(S)$—$NR_{11}R_{12}$, —$SO_2R_{10}$ group, wherein $R_{10}$ is independently selected from hydrogen, optionally substituted group selected from ($C_1$-$C_6$)alkyl, ($C_2$-$C_6$)alkenyl, ($C_2$-$C_6$)alkynyl, ($C_3$-$C_7$)cycloalkyl, aryl, heteroaryl, heterocyclyl group;
$R_{11}$ and $R_{12}$ is independently selected from hydrogen, optionally substituted group selected from ($C_1$-$C_6$)alkyl, ($C_1$-$C_6$)alkoxy, aryl or benzyl group;
In a preferred embodiment, the groups, radicals described above may be selected from:
"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but not are limited to methyl, ethyl, propyl, isopropyl, butyl, sec-butyl, tert.-butyl, pentyl, hexyl etc. Where the specified number of carbon atoms permits e.g. from C3-10, the term alkyl also includes cycloalkyl groups, and combinations of linear or branched alkyl chains combined with cycloalkyl structures. When no number of carbon atoms is specified, C(1-6) is intended.

"Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. Where the specified number of carbon atoms permits, e. g., from C5-10, the term alkenyl also includes cycloalkenyl groups and combinations of linear, branched and cyclic structures. When no number of carbon atoms is specified, C(2-6) is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, is intended.

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

"Cycloalkyl" is the subset of alkyl and means saturated carbocyclic ring having a specified number of carbon atoms, preferably 3-6 carbon atoms. Examples of cycloalkyl include cyclopropyl, cyclobutyl, cyclopentyl, cyclohexyl, cycloheptyl etc. A cycloalkyl group generally is monocyclic unless otherwise stated. Cycloalkyl groups are saturated unless and otherwise stated.

The "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocyclyl" means a saturated, partially saturated or unsaturated aromatic or non-aromatic mono, bi or tricyclic radicals, containing one or more heteroatoms selected from nitrogen, sulfur and oxygen, further optionally including the oxidized forms of sulfur, namely SO & $SO_2$. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above; "Heteroaryl" means an aromatic or partially aromatic heterocycle that contains at least one ring heteroatom selected from O, S and N. Heteroaryls thus include heteroaryls fused to the other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl etc. For heterocyclyl; and heteroaryl groups, rings and ring systems containing from 3-15 carbon atoms are included, forming 1-3 rings.

The term "haloalkyl" means a alkyl structure in which at least one hydrogen is replaced with a halogen atom. In certain embodiments in which two or more hydrogen atoms are replaced with halogen atoms, the halogen atoms are all the same as one another.

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogen on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. Such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromie, hydrochloric, hydroiodide, hydroxymaleic, hydroxynaphthoic, isethionic, lactic, lactobionic, -lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from but not limited to the following:

N'-cyano-N-((1,2,3,5,6,7-hexahydro-s-indacen-4-yl)carbamoyl)-4-methylbenzene sulfonimidamide;

N'-cyano-N-((1,2,3,5,6,7-hexahydro-s-indacen-4-yl)carbamoyl)-4-methylbenzene sulfonimidamide;

N'-cyano-N-((2,6-diisopropylphenyl)carbamoyl)-4-methylbenzenesulfonimidamide;

N-((1,2,3,5,6,7-hexahydro-s-indacen-4-yl)carbamoyl)-4-methylbenzenesulfonimidamide;

N-((2,6-diisopropylphenyl)carbamoyl)-4-methylbenzenesulfonimidamide;

N-((2,6-diisopropylphenyl)carbamoyl)-4-methyl-N'-(2,2,2-trifluoroethyl)benzenesulfonimidamide;

N-((1,2,3,5,6,7-hexahydro-s-indacen-4-yl)carbamoyl)-4-methyl-N'-(2,2,2-trifluoroethyl)-benzenesulfonimidamide;

N-((2,6-diisopropylphenyl)carbamoyl)-N'-methoxy-4-methylbenzenesulfonimidamide;

N-((1,2,3,5,6,7-hexahydro-s-indacen-4-yl)carbamoyl)-N'-isopropyl-4-methylbenzenesulfonimidamide;

N-((2,6-diisopropylphenyl)carbamoyl)-N'-isopropyl-4-methylbenzenesulfonimidamide;

N-((1,2,3,5,6,7-hexahydro-s-indacen-4-yl)carbamoyl)-N'-methoxy-4-methylbenzenesulfonimidamide;

N-((1,2,3,5,6,7-hexahydro-s-indacen-4-yl)carbamoyl)-N',4-dimethylbenzenesulfonimidamide;

N-((1,2,3,5,6,7-hexahydro-s-indacen-4-yl)carbamoyl)-4-methyl-N'-(1H-pyrazol-5-yl)benzenesulfonimidamide;

N'-(4-fluorophenyl)-N-((1,2,3,5,6,7-hexahydro-s-indacen-4-yl)carbamoyl)-4-methylbenzenesulfonimidamide;

N-((1,2,3,5,6,7-hexahydro-s-indacen-4-yl)carbamoyl)-4-methyl-N'-(pyridin-2-yl)benzenesulfonimidamide;

4-acetyl-N'-cyano-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)-4-(2-hydroxypropan-2-yl)benzenesulfonimidamide;

N'-cyano-N-((1,2,3,5,6,7-hexahydro-s-indacen-4-yl)carbamoyl)-3-nitrobenzenesulfonimidamide;

N'-cyano-N-((1,2,3,5,6,7-hexahydro-s-indacen-4-yl)carbamoyl)-4-methoxybenzenesulfonimidamide;

N'-cyano-N-((2,6-diisopropylphenyl)carbamoyl)-4-methoxybenzenesulfonimidamide;

N'-cyano-4-fluoro-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)benzenesulfonimidamide;

N-((3-(1,2,3,5,6,7-hexahydro-s-indacen-4-yl)ureido)(oxo)(p-tolyl)-l6-sulfanylidene)-methanesulfonamide;

N'-cyano-N-((1,2,3,5,6,7-hexahydro-s-indacen-4-yl)carbamoyl)-6-methoxypyridine-3-sulfonimidamide;

N'-cyano-3-fluoro-N-((1,2,3,5,6,7-hexahydro-s-indacen-4-yl)carbamoyl)-4-methylbenzenesulfonimidamide;

4-chloro-N'-cyano-N-((1,2,3,5,6,7-hexahydro-s-indacen-4-yl)carbamoyl)benzenesulfonimidamide;

4-bromo-N'-cyano-N-((1,2,3,5,6,7-hexahydro-s-indacen-4-yl)carbamoyl)benzenesulfonimidamide;

4-(benzyloxy)-N'-cyano-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)-4-(trifluoromethyl)-benzenesulfonimidamide;

N'-cyano-N-((1,2,3,5,6,7-hexahydro-s-indacen-4-yl)carbamoyl)pyridine-2-sulfonimidamide;

Ethyl ((3-(1,2,3,5,6,7-hexahydro-s-indacen-4-yl)ureido)(oxo)(p-tolyl)-$\lambda^6$-sulfaneylidene)-carbamate;

N-((3-(1,2,3,5,6,7-hexahydro-s-indacen-4-yl)ureido)(oxo)-(p-tolyl)-$\lambda^6$-sulfaneylidene)-acetamide;

N'-carbamoyl-N-((1,2,3,5,6,7-hexahydro-s-indacen-4-yl)carbamoyl)-4-methylbenzenesulfonimidamide;

N'-cyano-N-((1,2,3,5,6,7-hexahydro-s-indacen-4-yl)carbamoyl)-3-(2-hydroxypropan-2-yl)benzenesulfonimidamide;

N'-cyano-N-((1,2,3,5,6,7-hexahydro-s-indacen-4-yl)carbamoyl)-4-(3-hydroxyoxetan-3-yl)benzenesulfonimidamide;

N'-cyano-N-((1,2,3,5,6,7-hexahydro-s-indacen-4-yl)carbamoyl)-4-(prop-1-en-2-yl)furan-2-sulfonimidamide;

5-bromo-N'-cyano-N-((1,2,3,5,6,7-hexahydro-s-indacen-4-yl)carbamoyl)thiophene-2-sulfonimidamide;

N'-cyano-N-((1,2,3,5,6,7-hexahydro-s-indacen-4-yl)carbamoyl)-3-methoxybenzenesulfonimidamide;

N'-cyano-N-((1,2,3,5,6,7-hexahydro-s-indacen-4-yl)carbamoyl)-4-(2-hydroxypropan-2-yl)furan-2-sulfonimidamide N'-cyano-N-((1,2,3,5,6,7-hexahydro-s-indacen-4-yl)carbamoyl)-2,3-dihydrobenzo[b][1,4]dioxine-6-sulfonimidamide;

N'-cyano-N-((1,2,3,5,6,7-hexahydro-s-indacen-4-yl)carbamoyl)-5-(2-hydroxypropan-2-yl)thiophene-2-sulfonimidamide;

N'-cyano-2-fluoro-N-((1,2,3,5,6,7-hexahydro-s-indacen-4-yl)carbamoyl)-5-methylbenzenesulfonimidamide;

N'-cyano-3-(1,1,1,3,3,3-hexafluoro-2-hydroxypropan-2-yl)-N-((1,2,3,5,6,7-hexahydro-s-indacen-4-yl)carbamoyl)benzenesulfonimidamide N'-cyano-3,5-difluoro-N-((1,2,3,5,6,7-hexahydro-s-indacen-4-yl)carbamoyl)benzenesulfonimidamide;

N'-cyano-2,4-difluoro-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)-3-(trifluoromethoxy)-benzenesulfonimidamide;

N'-cyano-N-((2,6-diisopropylphenyl)carbamoyl)-3-(2-hydroxypropan-2-yl)benzenesulfonimidamide;

N'-cyano-N-((1,2,3,5,6,7-hexahydro-s-indacen-4-yl)carbamoyl)-1-phenylmethanesulfonimidamide;

N-((3-(1,2,3,5,6,7-hexahydro-s-indacen-4-yl)ureido)(3-(2-hydroxypropan-2-yl)phenyl)(oxo)-16-sulfaneylidene)methanesulfonamide;

N'-cyano-N-((1,2,3,6,7,8-hexahydro-as-indacen-4-yl)carbamoyl)-4-methylbenzenesulfonimidamide;

N'-cyano-N-((1,2,3,5,6,7-hexahydro-s-indacen-4-yl)carbamoyl)thiophene-2-sulfonimidamide;

N'-cyano-N-((1,2,3,5,6,7-hexahydro-s-indacen-4-yl)carbamoyl)-3,4-dimethoxybenzene-sulfonimidamide;

N'-cyano-N-((1,2,3,5,6,7-hexahydro-s-indacen-4-yl)carbamoyl)-6-methylpyridine-2-sulfonimidamide;

N'-cyano-N-((1,2,3,5,6,7-hexahydro-s-indacen-4-yl)carbamoyl)-6-methylpyridine-2-sulfonimidamide;

N',3-dicyano-N-((1,2,3,5,6,7-hexahydro-s-indacen-4-yl)car-
bamoyl)benzene-sulfonimidamide;
N'-cyano-N-((1,2,3,5,6,7-hexahydro-s-indacen-4-yl)car-
bamoyl)pyridine-3-sulfonimidamide
N',4-dicyano-N-((1,2,3,5,6,7-hexahydro-s-indacen-4-yl)car-
bamoyl)benzenesulfonimidamide;
N'-cyano-N-((1,2,3,5,6,7-hexahydro-s-indacen-4-yl)car-
bamoyl)pyridine-4-sulfonimidamide;
N'-cyano-3-fluoro-N-((1,2,3,5,6,7-hexahydro-s-indacen-4-
yl)carbamoyl)benzenesulfonimidamide;
N'-cyano-N-((1,2,3,5,6,7-hexahydro-s-indacen-4-yl)car-
bamoyl)quinoline-8-sulfonimidamide;
N'-cyano-N-((1,2,3,5,6,7-hexahydro-s-indacen-4-yl)car-
bamoyl)-4-morpholinobenzene sulfonimidamide;
N-(3-(N'-cyano-N-((1,2,3,5,6,7-hexahydro-s-indacen-4-yl)
carbamoyl)sulfamidimidoyl) phenyl) acetamide;
N'-cyano-N-((1,2,3,5,6,7-hexahydro-s-indacen-4-yl)car-
bamoyl)-3-morpholinobenzene sulfonimidamide;
N'-cyano-4-fluoro-N-((1,2,3,5,6,7-hexahydro-s-indacen-4-
yl)carbamoyl)-3-(2-hydroxypropan-2-yl)benzenesulfo-
nimidamide;
N'-cyano-2-fluoro-N-((1,2,3,5,6,7-hexahydro-s-indacen-4-
yl)carbamoyl)-5-(2-hydroxypropan-2-yl)benzenesulfo-
nimidamide;
N'-cyano-N-((1,2,3,5,6,7-hexahydro-s-indacen-4-yl)car-
bamoyl)-5-(2-hydroxypropan-2-yl)pyridine-3-sulfonimi-
damide;
N'-cyano-1-(4-cyanophenyl)-N-((1,2,3,5,6,7-hexahydro-s-
indacen-4-yl)carbamoyl)-methanesulfonimidamide;
1-(4-cyanophenyl)-N-((1,2,3,5,6,7-hexahydro-s-indacen-4-
yl)carbamoyl)methanesulfonimidamide;
N'-cyano-3-(2-hydroxypropan-2-yl)-N-((3-oxo-1,2,3,5,6,7-
hexahydro-s-indacen-4-yl)carbamoyl)-benzenesulfonimi-
damide.
or pharmaceutically acceptable salts of any of the com-
pounds above.

Following is a list of abbreviations used in the description of the preparation of the compounds of the present invention:

bs: broad singlet
CDCl$_3$: Deuterated chloroform
CHCl$_3$: Chloroform
d: doublet
dd: doublet of doublet
dt: doublet of triplet
DCM: Dichloromethane
DMAC: N,N-(Dimethylacetamide)
DMAP: 4-(Dimethylamino) pyridine
DMF: N,N-Dimethyl formamide
DMSO: Dimethyl sulfoxide
EDTA: Ethylenediaminetertraacetic acid
EtOAc: Ethyl acetate
EtOH: Ethanol
HCl(g): Hydrogen chloride (gas)
K$_2$CO$_3$: Potassium carbonate
MeOH: Methanol
m: multiplet
mmol: millimoles
µg: microgram
MS: Mass spectrum
Na$_2$CO$_3$: Sodium carbonate
ng: nanogram
NIS: N-iodosuccinimide
$^1$H NMR: Proton nuclear magnetic resonance
POCl$_3$: Phosphorylchloride
s: singlet
t: Triplet
td: triplet of doublet
THF: Tetrahydrofuran
TLC: Thin layer chromatography RT: room temperature
N$_2$: Nitrogen
PMA = Phorbol 12-myristate 13-acetate
IL1β: Interleukin 1 beta
TNF α: Tumor necrosis factor alpha
DAMP: damage-associated molecular pattern;
PAMP: pathogen-associated molecular pattern;
TLR: Toll-like receptor.

General Process for Preparation

The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include, but not limited to those described below, where all symbols are as defined earlier unless and otherwise defined below.

The compounds of the general formula (I) can be prepared as described in schemes below along with suitable modifications/variations which are well within the scope of a person skilled in the art.

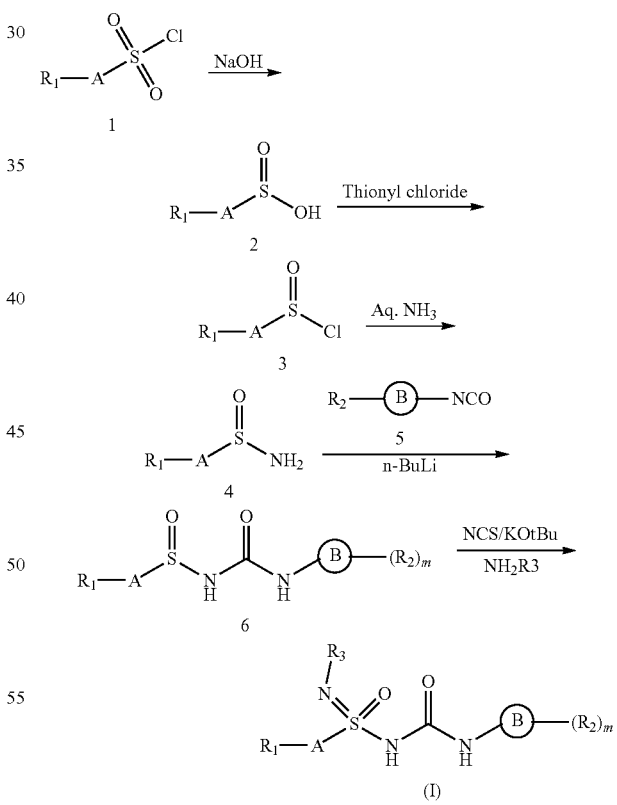

Wherein A, B, R$_1$, R$_2$, and R$_3$, are as defined earlier. Compound 2 can be prepared by variety of methods familiar to those skilled in art using a base like sodium hydroxide from commercially available sulfonyl chloride (1). Chlorination of 2 with reagents like thionyl chloride afforded 3. Compound 3 on treatment with ammonia under suitable conditions and appropriate solvents provided compound 4.

Compound 4 on treatment with isocyanato derivative (5) under suitable conditions, in presence of base like butyl lithium and appropriate solvents provided compound of formula 6. Compound 6 was subjected to chlorination with suitable reagent under suitable conditions, base and solvent followed by reaction with optionally substituted amines to afford compounds of formula (I). Chiral separation of the compounds of formula (I) can be achieved using suitable chiral columns via techniques like HPLC; or by using suitable chiral reagents, by a person skilled in the art.

The invention is further illustrated by the following non-limiting examples which describe the preferred way of carrying out the present invention. These are provided without limiting the scope of the present invention in any way.

$^1$H NMR spectral data given in the examples (vide infra) are recorded using a 400 MHz spectrometer (Bruker AVANCE-400) and reported in δ scale. Until and otherwise mentioned the solvent used for NMR is CDCl$_3$ using TMS as the internal standard.

Example-1: Preparation of N'-cyano-N-((2,6-diisopropylphenyl)carbamoyl)-4-methyl benzene sulfonimidamide Intermediate-1: Preparation 4-methylbenzenesulfinic Acid

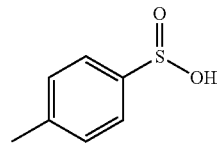

Sodium sulfite (12.64 g, 100 mmol) was dissolved in water (50 mL) at room temperature; it was heated to 65° C. temp. 10 M solution of NaOH (7.22 g, 181 mmol) was added drop wise. At the same time p-toluenesulfonyl chloride (15.3 g, 80 mmol) was added portion wise. After the addition the reaction mixture was heated to 70° C. for 3 hours. After completion of starting material, hot solution was filtered and the filtrate was kept the fridge for 17 hours. Solid was ppt. out, filtered it. Then solid was dissolved in water (120 mL) and cooled to 0° C. temp., acidified with conc. HCl. stirred for 1 hour. and solid was filtered off, washed it with cold water (5 mL×3) and dried under desiccator over P$_2$O$_5$ to yield 4-methylbenzenesulfinic acid (8.0 g, 51.2 mmol, 63.8% yield)

$^1$H NMR (400 MHz, CDCl$_3$): δ=7.63 (d, 2H), 7.38 (d, 2H), 2.42 (s, 3H); MS (ESI): m/z (%)=154.4 (100%) (M-H)$^-$.

Intermediate 2: Preparation of 4-methylbenzene-1-sulfinic chloride

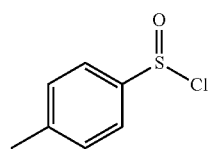

4-methylbenzenesulfinic acid (10.0 g, 64.0 mmol) was taken in ether (50 mL), slurry was cooled to 0° C. and added thionyl chloride (18.69 ml, 256 mmol) drop wise. After the addition was completed, ice bath was removed and reaction mixture was heated to 40° C. for 4 hours. Upon completion of starting material, reaction mixture was concentrated under reduced pressure to obtain crude 4-methylbenzene-1-sulfinic chloride (11.18 g, 64.0 mmol, 100% yield). It was directly used in the next step without further purification.

Intermediate 3

Step 1: Preparation of 4-methylbenzenesulfinamide

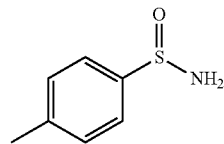

4-methylbenzene-1-sulfinic chloride (11 g, 63.0 mmol) was dissolved in ether (50 mL), it was cooled to 0° C. and ammonia gas was purged for 45 min. Upon completion of starting material, reaction mixture was concentrated under reduced pressure. Then into it water was added, solid was filtered off and washed with water. The obtained solid was dried under reduced pressure in dessicator over P$_2$O$_5$ to yield 4-methylbenzenesulfinamide (7.6 g, 49.0 mmol, 78% yield)

$^1$H NMR (400 MHz, CDCl$_3$): δ=7.65 (d, 2H), 7.33 (d, 2H), 4.29 (s, 2H), 2.43 (s, 3H); MS (ESI): m/z (%)=155.33 (100%) (M+H)$^+$

Intermediate 4

Preparation of N-((1,2,3,5,6,7-hexahydro-s-indacen-4-yl)carbamoyl)-4-methylbenzenesulfinamide

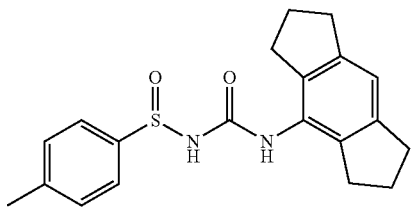 [SMILES: Cc1ccc(S(=O)NC(=O)Nc2c3c(cc4c2CCC4)CCC3)cc1]

4-methylbenzenesulfinamide (1 eq.) was dissolved in THF (20 mL) under N$_2$ atm. it was cooled to -78° C. and drop wise added n-butyl lithium (1.2 eq), after the addition solution was stirred for 30 min. at -78° C. temp. Then bath was removed and reaction mixture was stirred for 30 min. at RT. Then 4-isocyanato-1,2,3,5,6,7-hexahydro-s-indacene (1.2 eq.) was added drop wise at RT. Solid was ppt. then reaction mixture was further stirred for 4 h at RT. Upon completion of starting material, reaction mixture was concentrated under reduced pressure, resulting residue was treated with water (30 mL) solid was collected by filtration, it was washed with water and hexane, then dried under reduced pressure in dessicator over P$_2$O$_5$ to yield N-((1,2,3,5,6,7-hexahydro-s-indacen-4-yl)carbamoyl)-4-methylbenzenesulfinamide.

13

Compound-1

N'-cyano-N-((1,2,3,5,6,7-hexahydro-s-indacen-4-yl)carbamoyl)-4-methylbenzene sulfonimidamide

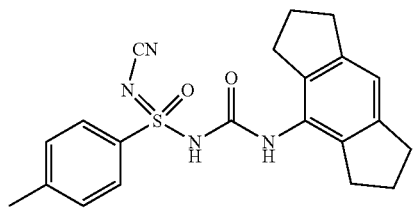 [SMILES: Cc1ccc(S(=O)(=NC#N)NC(=O)Nc2c3c(cc4c2CCC4)CCC3)cc1]

N-((1,2,3,5,6,7-hexahydro-s-indacen-4-yl)carbamoyl)-4-methylbenzenesulfinamide (1.0 eq.) was taken in MeCN (10 mL) under N2 atm. Solid cyanamide (2.1 eq.), potassium tert-butoxide (2 eq.) and N-Chlorosuccinimide (1.2 eq.) were added subsequently. The resulted suspension was stirred further for 3 h at RT. Upon completion of starting material, reaction mixture was concentrated under reduced pressure. it was diluted with Ethyl Acetate (15 mL) and water, layers were separated, aq. layer was back extracted with Ethyl Acetate (15 mL×4), all org. layer was combined and washed with water (15 mL), brine (15 mL), dried it over $Na_2SO_4$ and conc. under reduced pressure at 45° C. to yield crude product, which was purified by preparative HPLC to afford N'-cyano-N-((1,2,3,5,6,7-hexahydro-s-indacen-4-yl)carbamoyl)-4-methylbenzene sulfonimidamide.

$^1$H NMR (400 MHz, DMSO-$d_6$): δ=7.91 (s, 1H), 7.65 (d, J=8.0 Hz, 2H), 7.27 (d, J=8.0 Hz, 2H), 6.78 (s, 1H), 2.75-2.67 (m, 4H), 2.65-2.56 (m, 4H), 2.34 (s, 3H), 1.92-1.83 (m, 4H); MS (ESI): m/z (%)=395.10 (100%) (M+H)$^+$, 393.15 (100%) (M+H)

Alternatively, the compounds of the general formula (I) can be prepared as described in schemes below along with suitable modifications/variations which are well within the scope of a person skilled in the art.

Scheme 2

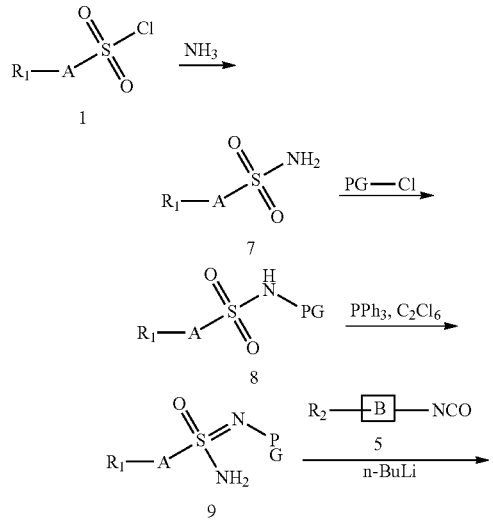

14

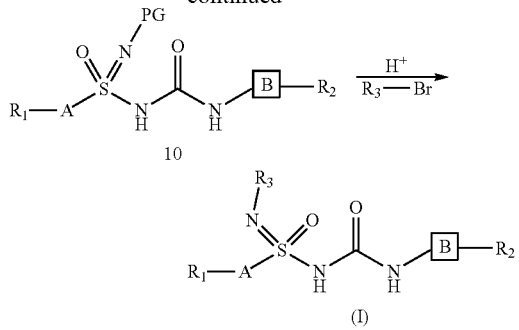

Wherein PG is selected from silyl groups like tert-butyldiphenylsilyl, tert-butyldimethylsilyl, trimethylsilyl or 9-Fluorenylmethyl carbamate, FMOC (Fluorenylmethyloxycarbonyl), t-Butyl carbamate, BOC; Benzyl carbamate, Acetamide, Benzylamine, p-Toluenesulfonamide. A, B, $R_1$, $R_2$, and $R_3$, are as defined earlier. Compound 7 can be prepared by using ammonia from commercially available sulfonyl chloride (1). Protection of amine group of 7 with suitable protecting groups like substituted silyl chlorides afforded 8. Compound 8 on treatment with triphenyl phosphine and dichloroethane under suitable conditions and appropriate solvents provide compound of compound 9. Compound 9 on treatment with isocyanato derivative (5) under suitable conditions, base like butyl lithium and appropriate solvents yielded compound of formula 10. Compound 10 was subjected to the deprotection with suitable reagent under suitable conditions, followed by reaction with optionally substituted halides provide compounds of formula (I). Chiral separation of the compounds of formula (I) can be achieved using suitable chiral columns via techniques like HPLC; or by using suitable chiral reagents, by a person skilled in the art.

The invention is further illustrated by the following non-limiting examples which describe the preferred way of carrying out the present invention. These are provided without limiting the scope of the present invention in any way.

Example-2: Preparation of N'-cyano-N-((2,6-diisopropylphenyl)carbamoyl)-4-methyl benzene sulfonimidamide Intermediate-1: Preparation N-(tert-butyldimethylsilyl)-4-methylbenzenesulfonamide

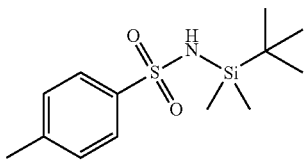 [SMILES: Cc1ccc(S(=O)(=O)N[Si](C)(C)C(C)(C)C)cc1]

4-methylbenzenesulfonamide (10.0 g, 58.4 mmol, 1 eq.) was taken in THF (50 mL), and added triethyl amine (17.41 mL, 128 mmol, 2.2 eq.) drop wise at 0° C., further a solution of tert-butylchlorodimethylsilane (11.0 g, 73 mmol, 1.25 eq.) in toluene (10 mL) was added. After the addition completed, ice bath was removed and reaction mixture was heated to 50° C. for 16 h. Upon completion of starting material, reaction mixture was concentrated under reduced pressure. Subsequently it was diluted with EA (100 mL) and water, layers were separated, aq. layer was back extracted with EA (50 mL×4), all org. layer was combined and washed with water (50 mL), brine (50 mL), dried over Na$_2$SO$_4$ and conc. under reduced pressure at 45° C. to yield crude product, which was purified by column chromatography to afford N-(tert-butyldimethylsilyl)-4-methylbenzenesulfonamide (12 g, 72% yield)

$^1$H NMR (DMSO-d$_6$, 400 MHz) δ ppm: 7.69 (d, 2H, J=6.4 Hz), 7.58 (s, 1H), 7.36 (d, 2H, J=8.4 Hz), 2.37 (s, 3H), 0.86 (s, 9H), 0.08 (s, 6H); MS (ESI): m/z (%)=285.9 (80%) (M+H)$^+$ Intermediate 2: Preparation of N'-(tert-butyldimethylsilyl)-4-methylbenzenesulfonimidamide

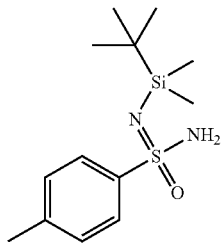

A solution of triphenylphosphane (5.05 g, 19.2 mmol, 1.1 eq.) and hexachloro ethane (4.56 g, 19.2 mmol, 1.1 eq.) in chloroform (50 mL) was heated to 70° C. for 5 h. Reaction mixture was cooled to 0° C. and added triethy amine (2.66 g, 26.3 mmol, 1.5 eq.) further a solution of N-(tert-butyldimethylsilyl)-4-methylbenzenesulfonamide (5.0 g, 17.51 mmol, 1.0 eq.) in chloroform (10 mL) was added. After 20 minutes at 0° C., ammonia gas was purged. Reaction mixture was concentrated to yield crude product, which was purified by column chromatography to afford N'-(tert-butyldimethylsilyl)-4-methylbenzenesulfon-imidamide (3.2 g, 64% yield)

$^1$H NMR (DMSO-d$_6$, 400 MHz) δ ppm: 7.54-7.73 (m, 2H), 7.30 (d, 2H, J=8 Hz), 6.57 (s, 2H), 2.35 (s, 3H), 0.87 (s, 9H), 0.00 (s, 6H); MS (ESI): m/z (%)=284.9 (100%) (M+H)$^+$.

Intermediate 3: Preparation of N'-(tert-butyldimethylsilyl)-N-((1,2,3,5,6,7-hexahydro-s-indacen-4-yl)carbamoyl)-4-methylbenzenesulfonimidamide

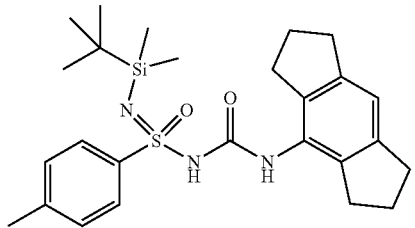 [SMILES: Cc1ccc(S(=O)(=N[Si](C)(C)C(C)(C)C)NC(=O)Nc2c3c(cc4c2CCC4)CCC3)cc1]

To a solution of N'-(tert-butyldimethylsilyl)-4-methylbenzenesulfon-imidamide (1.7 g, 5.98 mmol, 1.0 eq.) in dry THF (25 mL) was added n-BuLi (2.87 mL, 2.5 M, 7.17 mmol, 1.2 eq.) at −78° C. The reaction mixture was stirred at this temperature for 0.5 h and at rt for 0.5 h. 4-isocyanato-1,2,3,5,6,7-hexahydro-s-indacene (1.19 g, 5.98 mmol, 1.0 eq.) was added to the reaction mixture at room temperature (RT) and stirred for 2 h. Reaction mixture was cooled to 0° C. and quenched with NH$_4$Cl. It was diluted with EA (100 mL) and water, layers were separated, aq. layer was back extracted with EA (50 mL×4), all org. layer was combined and washed with water (50 mL), brine (50 mL), dried it over Na2SO4 and conc. under reduced pressure at 45° C. to yield, crude product, which was used for next step.

$^1$H NMR (DMSO-d$_6$, 400 MHz) δ ppm: 9.93 (s, 1H), 8.06 (s, 1H), 7.82 (d, 2H, J=8 Hz), 7.37 (d, 2H, J=8 Hz), 6.90 (s, 1H), 2.78-2.67 (m, 4H), 2.56-2.50 (m, 4H), 2.35 (s, 3H), 1.95-1.91 (m, 4H), 0.90 (s, 9H), 0.00 (s, 6H); MS (ESI): m/z (%)=484.5 (100%) (M+H)$^+$ Intermediate 4: Preparation of N-((1,2,3,5,6,7-hexahydro-s-indacen-4-yl)carbamoyl)-4-methylbenzenesulfonimidamide

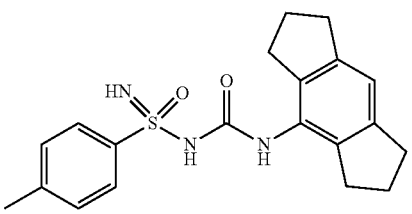 [SMILES: Cc1ccc(S(=N)(=O)NC(=O)Nc2c3c(cc4c2CCC4)CCC3)cc1]

To a solution of N'-(tert-butyldimethylsilyl)-N-((1,2,3,5,6,7-hexahydro-s-indacen-4-yl)carbamoyl)-4-methylbenzenesulfonimidamide (3.3 g, 6.82 mmol, 1.0 eq.) in dry THF (35 mL) was added HCl-dioxane (5.12 mL, 4 M, 7.17 mmol, 3 eq.) at 0° C. The reaction mixture was stirred at this temperature for 0.5 h and at RT for 1 h. Reaction mixture was cooled to 0° C. and quenched with aq. ammonia and waster was added. This mixture was filtered and dried under vacuum to yield N-((1,2,3,5,6,7-hexahydro-s-indacen-4-yl)carbamoyl)-4-methylbenzenesulfonimidamide as white solid (2.2 g, Yield=87%)

$^1$H NMR (400 MHz, DMSO-d$_6$): δ=9.42 (s, 1H), 7.54 (d, J=7.6 Hz, 2H), 7.34 (d, J=7.6 Hz, 2H), 6.92 (s, 1H), 6.2 (bs, 2H), 2.82-2.79 (m, 8H), 2.36 (s, 3H), 1.82-1.72 (m, 4H); MS (ESI): m/z (%)=370.00 (100%) (M+H)$^+$, 368.05 (100%) (M−H)$^-$

Compound-2

N'-cyano-N-((1,2,3,5,6,7-hexahydro-s-indacen-4-yl)carbamoyl)-4-methylbenzene sulfonimidamide

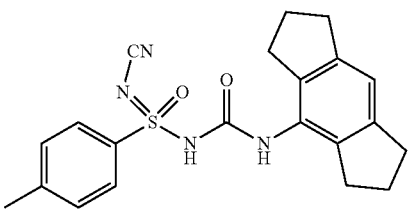 [SMILES: Cc1ccc(S(=O)(=NC#N)NC(=O)Nc2c3c(cc4c2CCC4)CCC3)cc1]

To a solution of N-((1,2,3,5,6,7-hexahydro-s-indacen-4-yl)carbamoyl)-4-methylbenzenesulfonimidamide (0.1 g, 0.27 mmol, 1.0 eq.) in DMF (1 mL) was added triethylamine (0.15 mL, 1.08 mmol, 4 eq.) and CNBr (0.057 g, 0.54 mmol, 2.0 eq.) at rt. The reaction mixture was stirred at room temperature for 18 h The crude product was purified by preparative HPLC to afford N'-cyano-N-((1,2,3,5,6,7-hexahydro-s-indacen-4-yl)carbamoyl)-4-methylbenzene sulfonimidamide (1.024 g, Yield=22%)

¹H NMR (400 MHz, DMSO-d₆): δ=7.91 (s, 1H), 7.65 (d, J=8.0 Hz, 2H), 7.27 (d, J=8.0 Hz, 2H), 6.78 (s, 1H), 2.75-2.67 (m, 4H), 2.65-2.56 (m, 4H), 2.34 (s, 3H), 1.92-1.83 (m, 4H); MS (ESI): m/z (%)=395.10 (100%) (M+H)⁺, 393.15 (100%) (M+H)

Using appropriate starting materials and suitable modifications of the process described in Example 2, including suitable addition and/or deletion of steps as may be necessary, well within the scope of a person skilled in the art, the following compounds were prepared in an analogues manner.

Example-3

N'-cyano-N-((2,6-diisopropylphenyl)carbamoyl)-4-methylbenzenesulfonimidamide

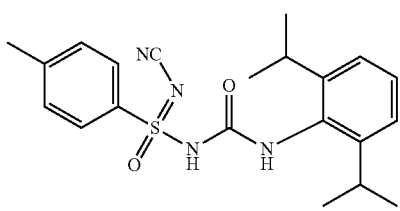 [SMILES: Cc1ccc(S(=O)(=NC#N)NC(=O)Nc2c(C(C)C)cccc2C(C)C)cc1]

¹H NMR (400 MHz, DMSO-d₆): δ=7.74 (s, 1H), 7.64 (d, J=8.0 Hz, 2H), 7.24 (d, J=8.0 Hz, 2H), 7.09 (t, J=8.0 Hz, 1H), 6.99 (d, J=8.0 Hz, 2H), 3.11 (sept, J=7.2 Hz, 2H), 2.33 (s, 3H), 1.08 (d, J=7.2 Hz, 12H); MS (ESI): m/z (%)=399.20 (100%) (M+H)⁺, 397.15 (100%) (M−H)⁻.

Example-4

N-((1,2,3,5,6,7-hexahydro-s-indacen-4-yl)carbamoyl)-4-methylbenzenesulfonimidamide

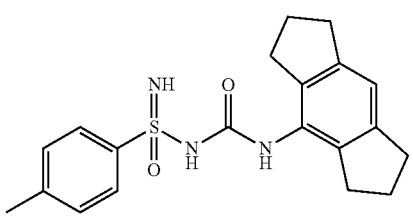 [SMILES: Cc1ccc(S(=N)(=O)NC(=O)Nc2c3c(cc4c2CCC4)CCC3)cc1]

¹H NMR (400 MHz, DMSO-d₆): δ=9.42 (s, 1H), 7.54 (d, J=7.6 Hz, 2H), 7.34 (d, J=7.6 Hz, 2H), 6.92 (s, 1H), 6.2 (bs, 2H), 2.82-2.79 (m, 8H), 2.36 (s, 3H), 1.82-1.72 (m, 4H); MS (ESI): m/z (%)=370.00 (100%) (M+H)⁺, 368.05 (100%) (M−H)⁻; IR (KBr): ν=3379, 3325, 3359, 3207, 2941, 2843, 1651, 1585, 1448, 1375, 1321, 1269 cm⁻¹.

Example-5

N-((2,6-diisopropylphenyl)carbamoyl)-4-methylbenzenesulfonimidamide

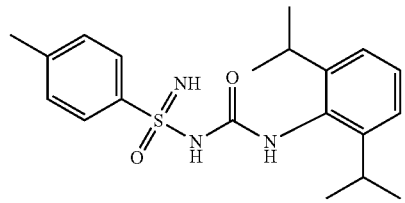 [SMILES: Cc1ccc(S(=N)(=O)NC(=O)Nc2c(C(C)C)cccc2C(C)C)cc1]

¹H NMR (400 MHz, DMSO-d₆): δ=9.69 (bs, 1H), 7.54 (bs, 2H), 7.35 (d, J=8.0 Hz, 2H), 7.19 (s, 1H), 7.08 (d, J=7.6 Hz, 2H), 6.23 (bs, 2H), 3.21 (bs, 2H), 2.36 (s, 3H), 1.06 (d, J=6.8 Hz, 6H), 0.86 (d, J=6.8 Hz, 6H); MS (ESI): m/z (%)=374.10 (100%) (M+H)⁺, 372.25 (100%) (M−H)⁻; IR (KBr): ν=3338, 3198, 3064, 2966, 2928, 2868, 1705, 1639, 1593, 1462, 1442, 1381, 1265, 1145 cm⁻¹.

Example-6

N-((2,6-diisopropylphenyl)carbamoyl)-4-methyl-N'-(2,2,2-trifluoroethyl)benzenesulfonimi-damide

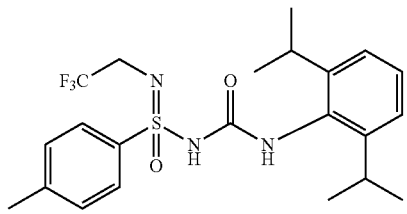 [SMILES: Cc1ccc(S(=O)(=NCC(F)(F)F)NC(=O)Nc2c(C(C)C)cccc2C(C)C)cc1]

¹H NMR (400 MHz, DMSO-d₆): δ=8.5 (s, 1H), 8.35 (s, 1H), 7.81 (d, J=8.4 Hz, 2H), 7.41 (d, J=8.0 Hz, 2H), 7.19-7.05 (m, 3H), 3.72 (bs, 2H), 3.08 (bs, 2H), 2.38 (s, 3H), 1.1 (d, J=6.4 Hz, 12H); MS (ESI): m/z (%)=456.17 (100%) (M+H)⁺; (KBr): ν=3396, 3142, 2958, 2866, 1616, 1483, 1274, 1242, 1170, 1085, 996 cm⁻¹.

Example-7

N-((1,2,3,5,6,7-hexahydro-s-indacen-4-yl)carbamoyl)-4-methyl-N'-(2,2,2-trifluoroethyl)-benzenesulfonimidamide

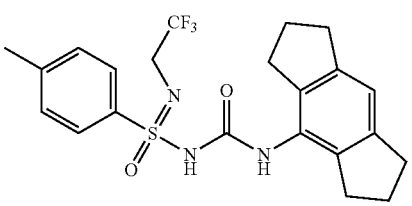 [SMILES: Cc1ccc(S(=O)(=NCC(F)(F)F)NC(=O)Nc2c3c(cc4c2CCC4)CCC3)cc1]

¹H NMR (400 MHz, DMSO-d₆): δ=8.5 (bs, 1H), 8.47 (s, 1H), 7.77 (bs, 2H),7.42 (d, J=8.0 Hz, 2H), 6.88 (s, 1H), 3.72

(bs, 2H), 2.79 (t, J=6.8 Hz, 4H), 2.68 (bs, 4H), 2.39 (s, 3H), 1.9 (t, J=7.2 Hz, 4H); MS (ESI): m/z (%)=452.20 (100%) (M+H)⁺.

Example-8

N-((2,6-diisopropylphenyl)carbamoyl)-N'-methoxy-4-methylbenzenesulfonimidamide

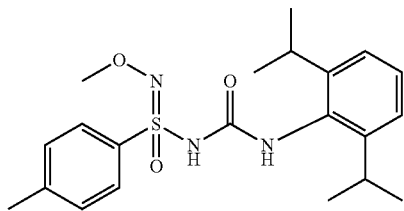 [SMILES: CON=S(=O)(NC(=O)Nc1c(C(C)C)cccc1C(C)C)c1ccc(C)cc1]

¹H NMR (400 MHz, DMSO-d₆): δ=9.82 (bs, 1H), 9.55 (s, 1H), 7.61 (d, J=8.0 Hz, 2H), 7.39 (d, J=8.0 Hz, 2H), 7.24 (t, J=7.6 Hz, 1H), 7.10 (d, J=7.2 Hz, 2H), 3.51 (s, 3H), 3.20 (bs, 2H), 2.43 (s, 3H), 1.06 (s, 6H), 0.74 (s, 6H); MS (ESI): m/z (%)=404.24 (100%) (M+H)⁺.

Example-9

N-((1,2,3,5,6,7-hexahydro-s-indacen-4-yl)carbamoyl)-N'-isopropyl-4-methylbenzenesulfonimidamide

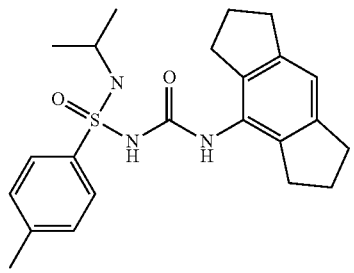

¹H NMR (400 MHz, DMSO-d₆): δ=9.35 (s, 1H), 7.54 (bs, 2H),7.35 (d, J=8.0 Hz, 2H), 6.93 (s, 1H), 6.81 (d, J=6.8 Hz, 1H), 3.67 (d, J=6.8 Hz, 1H), 2.80-2.71 (m, 6H), 2.37 (s, 3H), 2.20-2.19 (m, 2H), 1.91-1.82 (m, 4H), 1.06-1.01 (m, 6H); MS (ESI): m/z (%)=412.27 (100%) (M+H)⁺.

Example-10

N-((2,6-diisopropylphenyl)carbamoyl)-N'-isopropyl-4-methylbenzenesulfonimidamide

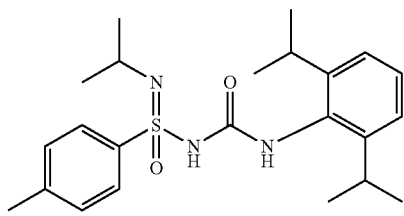 [SMILES: Cc1ccc(S(=O)(=NC(C)C)NC(=O)Nc2c(C(C)C)cccc2C(C)C)cc1]

¹H NMR (400 MHz, DMSO-d₆): δ=9.56 (s, 1H), 7.55 (d, J=8.0 Hz, 2H), 7.35 (d, J=7.6 Hz, 2H), 7.23 (t, J=6.4 Hz, 1H), 7.09 (d, J=7.6 Hz, 2H), 6.77 (d, J=8.0 Hz, 1H), 3.67 (d, J=7.2 Hz, 1H), 3.22 (bs, 2H), 2.36 (s, 3H), 1.07 (bs, 12H), 0.73 (s, 6H); MS (ESI): m/z (%)=416.30 (100%) (M+H)⁺.

Example-11

N-((1,2,3,5,6,7-hexahydro-s-indacen-4-yl)carbamoyl)-N'-methoxy-4-methylbenzenesulfonimidamide

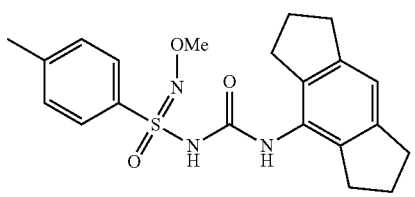 [SMILES: CON=S(=O)(NC(=O)Nc1c2c(cc3c1CCC3)CCC2)c1ccc(C)cc1]

¹H NMR (400 MHz, DMSO-d₆): δ=9.9 (bs, 1H), 9.35 (s, 1H), 7.58 (d, J=8.4 Hz, 2H), 7.38 (d, J=8.4 Hz, 2H), 6.95 (s, 1H), 3.52 (s, 3H), 2.73 (t, J=6.8 Hz, 4H), 2.39 (s, 3H), 2.53-2.22 (m, 4H), 1.85-1.66 (m, 4H); MS (ESI): m/z (%)=400.20 (100%) (M+H)⁺.

Example 12

N-((1,2,3,5,6,7-hexahydro-s-indacen-4-yl)carbamoyl)-N',4-dimethylbenzenesulfonimidamide

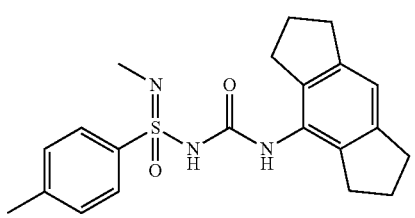 [SMILES: CN=S(=O)(NC(=O)Nc1c2c(cc3c1CCC3)CCC2)c1ccc(C)cc1]

¹H NMR (400 MHz, DMSO-d₆): δ=8.4 (bs, 1H), 7.73 (d, J=7.6 Hz, 2H), 7.42-7.36 (m, 3H), 6.87 (s, 1H), 2.79 (t, J=7.2 Hz, 4H), 2.70 (t, J=7.6 Hz, 4H), 2.39 (s, 6H), 1.96 (quin, J=7.6 Hz, 4H); MS (ESI): m/z (%)=384.10 (100%) (M+H)⁺; IR (KBr): v=3286, 3142, 2939, 2843, 1626, 1521, 1460, 1442, 1427, 1276, 1238, 1120 cm⁻¹.

Example-13

N-((1,2,3,5,6,7-hexahydro-s-indacen-4-yl)carbamoyl)-4-methyl-N'-(1H-pyrazol-5-yl)benzenesulfonimidamide

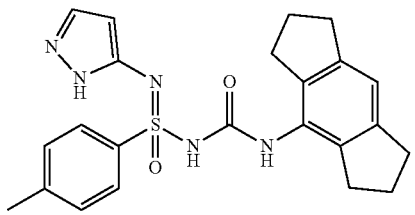 [SMILES: Cc1ccc(S(=O)(=Nc2ccn[nH]2)NC(=O)Nc2c3c(cc4c2CCC4)CCC3)cc1]

¹H NMR (400 MHz, DMSO-d₆): δ=12.09 (s, 1H), 9.33 (s, 1H), 7.64 (d, J=7.6 Hz, 2H), 7.50 (s, 1H), 7.37 (d, J=8.0 Hz, 2H), 6.96 (s, 1H), 6.30 (s, 1H), 2.76-2.67 (m, 6H), 2.39 (s, 3H), 2.21-2.17 (m, 2H), 1.87-1.84 (m, 4H); MS (ESI): m/z (%)=436.15 (100%) (M+H)⁺.

Example-14

N'-(4-fluorophenyl)-N-((1,2,3,5,6,7-hexahydro-s-indacen-4-yl)carbamoyl)-4-methylbenzenesulfonimidamide

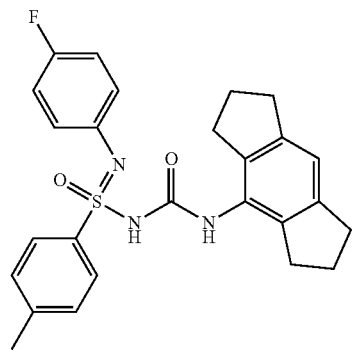 [SMILES: Cc1ccc(S(=O)(=Nc2ccc(F)cc2)NC(=O)Nc2c3c(cc4c2CCC4)CCC3)cc1]

¹H NMR (400 MHz, DMSO-d₆): δ=10.08 (bs, 1H), 8.35 (s, 1H), 7.71 (s, 2H), 7.36 (d, J=7.2 Hz, 2H), 7.07 (s, 4H), 6.89 (s, 1H), 2.79 (s, 4H), 2.67 (s, 4H), 2.35 (s, 4H), 1.95 (d, J=6.8 Hz, 4H); MS (ESI): m/z (%)=464.35 (100%) (M+H)⁺.

Example-15

N-((1,2,3,5,6,7-hexahydro-s-indacen-4-yl)carbamoyl)-4-methyl-N'-(pyridin-2-yl)benzenesulfonimidamide

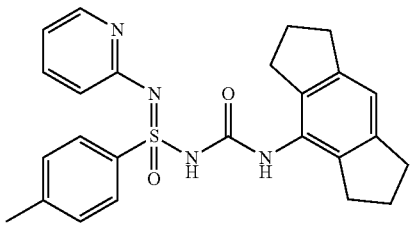 [SMILES: Cc1ccc(S(=O)(=Nc2ccccn2)NC(=O)Nc2c3c(cc4c2CCC4)CCC3)cc1]

¹H NMR (400 MHz, DMSO-d₆): δ=9.38 (bs, 1H), 8.23 (d, J=3.6 Hz, 1H), 7.87 (d, J=6.8 Hz, 1H), 7.70 (d, J=7.6 Hz, 3H), 7.39 (d, J=8.4 Hz, 2H), 7.00 (t, J=7.2 Hz, 2H), 2.80-2.73 (m, 6H), 2.39 (s, 3H), 2.24 (bs, 2H), 1.88-1.70 (m, 4H); MS (ESI): m/z (%)=447.25 (100%) (M+H)⁺.

Example-16

4-acetyl-N'-cyano-N-((1,2,3,5,6,7-hexahydro-s-indacen-4-yl)carbamoyl)benzenesulfonimidamide

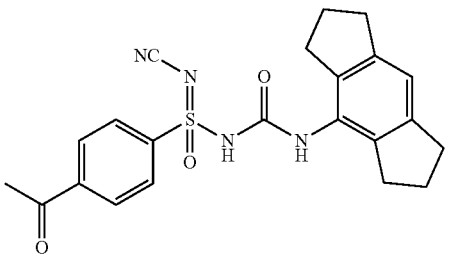 [SMILES: CC(=O)c1ccc(S(=O)(=NC#N)NC(=O)Nc2c3c(cc4c2CCC4)CCC3)cc1]

¹H NMR (400 MHz, DMSO-d₆): δ=8.1 (bs, 1H), 8.06 (d, J=8.4 Hz, 2H), 7.87 (d, J=8.4 Hz, 2H), 6.80 (s, 1H), 2.75-2.70 (m, 4H), 2.67-2.63 (m, 4H), 2.61 (s, 3H), 1.93 (t, J=7.2 Hz, 4H); MS (ESI): m/z (%)=423.10 (100%) (M+H)⁺; IR (KBr): ν=3433, 2949, 2845, 2189, 1687, 1599, 1541, 1263, 1199, 1118, 821 cm⁻¹.

Example-17

N'-cyano-N-((1,2,3,5,6,7-hexahydro-s-indacen-4-yl)carbamoyl)-4-(2-hydroxypropan-2-yl)benzenesulfonimidamide

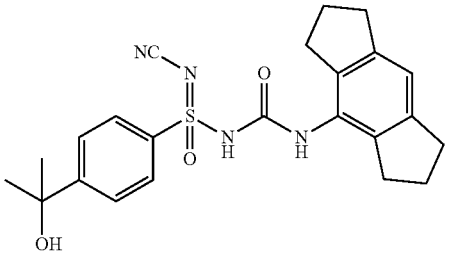 [SMILES: CC(C)(O)c1ccc(S(=O)(=NC#N)NC(=O)Nc2c3c(cc4c2CCC4)CCC3)cc1]

¹H NMR (400 MHz, DMSO-d₆): δ=8.0 (bs, 1H), 7.67 (d, J=8.4 Hz, 2H), 7.55 (d, J=8.4 Hz, 2H), 6.79 (s, 1H), 5.16 (s, 1H), 2.75 (t, J=7.2 Hz, 4H), 2.68-2.66 (m, 4H), 1.91 (t, J=7.2 Hz, 4H), 1.43 (s, 6H); MS (ESI): m/z (%)=439.15 (100%) (M+H)⁺.

Example-18

N'-cyano-N-((1,2,3,5,6,7-hexahydro-s-indacen-4-yl)carbamoyl)-3-nitrobenzenesulfonimidamide

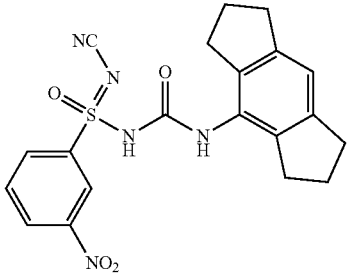 [SMILES: N#CN=S(=O)(NC(=O)Nc1c2c(cc3c1CCC3)CCC2)c1cccc([N+](=O)[O-])c1]

¹H NMR (400 MHz, DMSO-d₆): δ=8.48 (s, 1H), 8.37 (d, J=8.4 Hz, 2H), 8.17 (d, J=8.0 Hz, 2H), 7.82 (t, J=8.4 Hz, 2H), 6.80 (s, 1H), 2.78-2.69 (m, 4H), 2.68-2.57 (m, 4H), 1.98-1.81 (m, 4H); MS (ESI): m/z (%)=426.10 (100%) (M+H)⁺, 448.09 (15%) (M+Na).

Example-19

N'-cyano-N-((1,2,3,5,6,7-hexahydro-s-indacen-4-yl)carbamoyl)-4-methoxybenzenesulfonimidamide

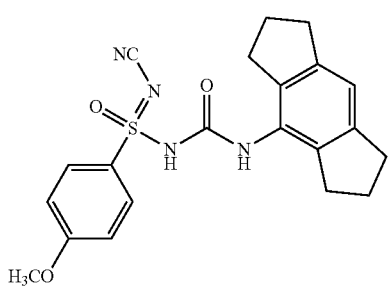 [SMILES: COc1ccc(S(=O)(=NC#N)NC(=O)Nc2c3c(cc4c2CCC4)CCC3)cc1]

¹H NMR (400 MHz, DMSO-d₆): δ=7.93 (s, 1H), 7.70 (d, J=9.2 Hz, 2H), 7.01 (d, J=8.8 Hz, 2H), 6.79 (s, 1H), 3.80 (s, 3H), 2.76 (t, J=7.6 Hz, 4H), 2.70-2.56 (m, 4H), 1.93-1.85 (m, 4H); MS (ESI): m/z (%)=411.19 (100%) (M+H)⁺, 433.17 (90%) (M+Na).

Example-20

N'-cyano-N-((2,6-diisopropylphenyl)carbamoyl)-4-methoxybenzenesulfonimidamide

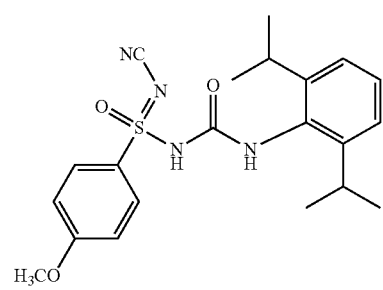 [SMILES: COc1ccc(S(=O)(=NC#N)NC(=O)Nc2c(C(C)C)cccc2C(C)C)cc1]

¹H NMR (400 MHz, DMSO-d₆): δ=7.55 (d, J=8.8 Hz, 2H), 7.48-7.44 (m, 2H); 7.13 (d, J=9.2 Hz, 2H), 3.83 (s, 3H), 3.06-3.00 (m, 1H), 2.21-2.14 (m, 1H), 1.37 (d, J=6.4 Hz, 3H), 1.17 (d, J=6.8 Hz, 3H), 0.944 (d, J=6.8 Hz, 3H), 0.194 (d, J=6.4 Hz, 3H); MS (ESI): m/z (%)=415.20 (100%) (M+H)⁺, 437.25 (10%) (M+Na); IR (KBr): ν=3464, 2972, 1595, 1525, 1410, 1267, 1147, 1014, 844, 557 cm⁻¹.

Example-21

N'-cyano-4-fluoro-N-((1,2,3,5,6,7-hexahydro-s-indacen-4-yl)carbamoyl)benzenesulfonimidamide

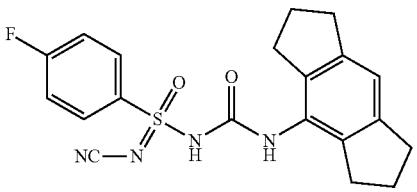 [SMILES: N#CN=S(=O)(NC(=O)Nc1c2c(cc3c1CCC3)CCC2)c1ccc(F)cc1]

¹H NMR (400 MHz, DMSO-d₆): δ=8.03 (br s, 1H), 7.81-7.77 (m, 2H), 7.32 (t, J=8.8 Hz, 2H), 6.79 (s, 1H), 2.73 (t, J=7.2 Hz, 4H), 2.64-2.59 (m, 4H), 1.90-1.87 (m, 4H); MS (ESI): m/z (%)=399.10 (100%) (M+H)⁺.

Example-22

N'-cyano-N-((1,2,3,5,6,7-hexahydro-s-indacen-4-yl)carbamoyl)benzenesulfonimidamide

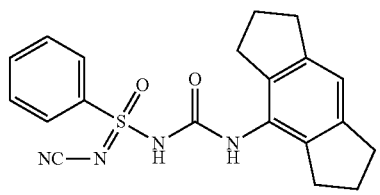 [SMILES: N#CN=S(=O)(NC(=O)Nc1c2c(cc3c1CCC3)CCC2)c1ccccc1]

¹H NMR (400 MHz, DMSO-d₆): δ=8.01 (br s, 1H), 7.77-7.75 (m, 2H), 7.49-7.46 (m, 3H), 6.79 (s, 1H), 2.76-2.72 (m, 4H), 2.67-2.60 (m, 4H), 1.93-1.89 (m, 4H).

Example-23

N-((3-(1,2,3,5,6,7-hexahydro-s-indacen-4-yl)ureido)(oxo)(p-tolyl)-16-sulfanylidene)-methanesulfonamide

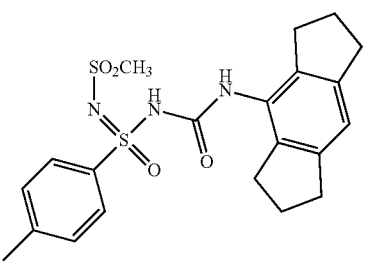 [SMILES: Cc1ccc(S(=O)(=NS(C)(=O)=O)NC(=O)Nc2c3c(cc4c2CCC4)CCC3)cc1]

¹H NMR (400 MHz, DMSO): δ=11.9 (bs, 1H), 7.8 (bs, 1H), 7.71 (d, J=8 Hz, 2H), 7.25 (d, J=8.4 Hz, 2H), 6.82 (s, 1H), 2.84 (s, 3H), 2.73-2.84 (m, 4H), 2.59-2.67 (m, 4H), 2.41 (s, 3H), 1.89-1.97 (m, 4H); MS (ESI): m/z (%)=448.35 (30%) (M+H)⁺; 465.3 (100%) (M+H₂O)⁺.

Example-24

N'-cyano-N-((1,2,3,5,6,7-hexahydro-s-indacen-4-yl)carbamoyl)-6-methoxypyridine-3-sulfonimidamide

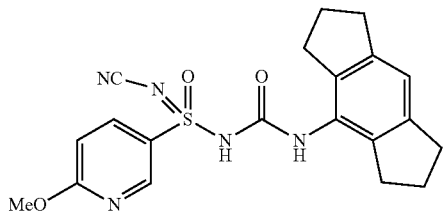 [SMILES: COc1ccc(S(=O)(=NC#N)NC(=O)Nc2c3c(cc4c2CCC4)CCC3)cn1]

$^1$H NMR (400 MHz, DMSO-d$_6$): δ=8.51-8.48 (m, 1H), 8.04 (br s, 1H), 8.01-7.93 (m, 1H), 6.92 (d, J=9.2 Hz, 1H), 6.80 (s, 1H), 3.87 (s, 3H), 2.81-2.59 (m, 8H), 1.91-1.84 (m, 4H); MS (ESI): m/z (%)=412.20 (100%) (M+H)$^+$.

Example-25

N'-cyano-3-fluoro-N-((1,2,3,5,6,7-hexahydro-s-indacen-4-yl)carbamoyl)-4-methylbenzenesulfonimidamide

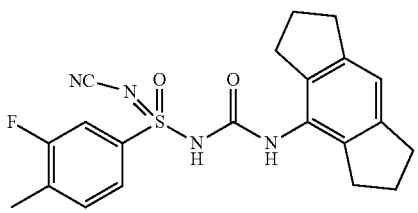 [SMILES: Cc1ccc(S(=O)(=NC#N)NC(=O)Nc2c3c(cc4c2CCC4)CCC3)cc1F]

$^1$H NMR (400 MHz, DMSO-d$_6$): δ=8.08 (br s, 1H), 7.49-7.47 (m, 1H), 7.43-7.39 (m, 2H), 6.80 (s, 1H), 2.73 (d, J=7.2 Hz, 4H), 2.68-2.58 (m, 4H), 2.28 (s, 3H), 1.93-1.88 (m, 4H); MS (ESI): m/z (%)=413.15 (100%) (M+H)$^+$; IR (KBr): ν=3433, 3234, 2951, 2193, 1599, 1577, 1533, 1492 cm$^{-1}$.

Example-26

4-chloro-N'-cyano-N-((1,2,3,5,6,7-hexahydro-s-indacen-4-yl)carbamoyl)benzenesulfonimidamide

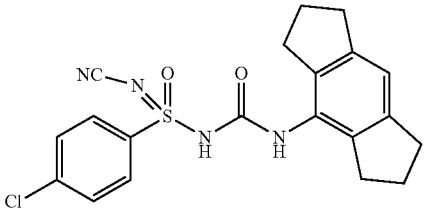 [SMILES: N#CN=S(=O)(NC(=O)Nc1c2c(cc3c1CCC3)CCC2)c1ccc(Cl)cc1]

$^1$H NMR (400 MHz, DMSO-d$_6$): δ=8.05 (br s, 1H), 7.74 (d, J=8.8 Hz, 2H), 7.56 (d, J=8.8 Hz, 2H), 6.80 (s, 1H), 2.74 (t, J=7.2 Hz, 4H), 2.68-2.59 (m, 4H), 1.93-1.87 (m, 4H); MS (ESI): m/z (%)=415.10 (100%) (M+H)$^+$; IR (KBr): ν=3257, 2945, 2845, 2189, 1678, 1597, 1535 cm$^{-1}$.

Example-27

4-bromo-N'-cyano-N-((1,2,3,5,6,7-hexahydro-s-indacen-4-yl)carbamoyl)benzenesulfonimidamide

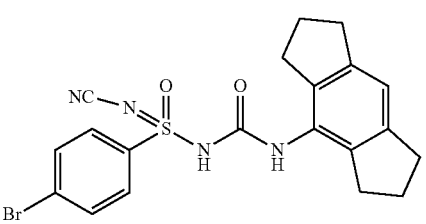 [SMILES: N#CN=S(=O)(NC(=O)Nc1c2c(cc3c1CCC3)CCC2)c1ccc(Br)cc1]

$^1$H NMR (400 MHz, DMSO-d$_6$): δ=8.06 (br s, 1H), 7.71-7.66 (m, 4H), 6.80 (s, 1H), 2.74 (t, J=7.2 Hz, 4H), 2.68-2.59 (m, 4H), 1.93-1.84 (m, 4H); MS (ESI): m/z (%)=459.15 (100%) (M)$^+$; IR (KBr): ν=3433, 3236, 2945, 2843, 2191, 1599, 1573, 1531 cm$^{-1}$.

Example-28

4-(benzyloxy)-N'-cyano-N-((1,2,3,5,6,7-hexahydro-s-indacen-4-yl)carbamoyl)benzenesulfonimidamide $^1$H NMR (400 MHz, DMSO-d$_6$): δ=7.91 (s, 1H), 7.70-7.66 (m, 2H), 7.47-7.45 (m, 2H), 7.42-7.38 (m, 2H), 7.36-7.32 (m, 2H), 7.10-7.05 (m, 3H), 6.79 (s, 1H), 5.16 (s, 1H), 3.34-2.68 (m, 4H), 2.67-2.90 (m, 4H), 1.91-1.89 (m, 4H); MS (ESI): m/z (%)=487.35 (100%) (M+H)$^+$, 509.45 (30%) (M+NH$_4$)$^+$; 485.55 (100%) (M−1); IR (KBr): ν=3223, 2947, 2177, 1593, 1496, 1251, 1114, 1095, 827. 698, 532 cm$^{-1}$.

Example-29

N'-cyano-N-((1,2,3,5,6,7-hexahydro-s-indacen-4-yl)carbamoyl)-4-(trifluoromethyl)-benzenesulfonimidamide

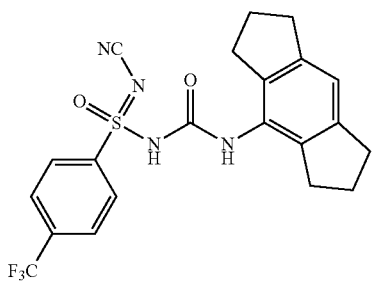 [SMILES: N#CN=S(=O)(NC(=O)Nc1c2c(cc3c1CCC3)CCC2)c1ccc(C(F)(F)F)cc1]

¹H NMR (400 MHz, DMSO-d₆, D2O—X): δ=8.12 (br, s, 1H), 7.94 (d, J=8.4 Hz, 2H), 7.88 (d, J=8.4 Hz, 2H), 6.80 (s, 1H), 2.75-2.72 (m, 4H), 2.68-2.55 (m, 4H), 1.91-1.87 (m, 4H); MS (ESI): m/z (%)=449.10 (100%) (M+H)⁺, 471.15 (30%) (M+Na)⁺, 447.30 (70%) (M−1)⁺; IR (KBr): ν=3433, 3248, 2195, 1600, 1402, 1323, 1132, 1062, 827, 709 cm⁻¹.

Example-30

N'-cyano-N-((1,2,3,5,6,7-hexahydro-s-indacen-4-yl)carbamoyl)pyridine-2-sulfonimidamide

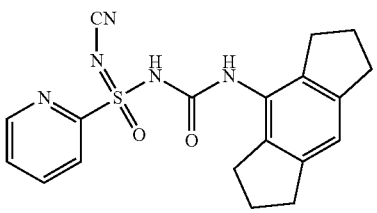 [SMILES: N#CN=S(=O)(NC(=O)Nc1c2c(cc3c1CCC3)CCC2)c1ccccn1]

¹H NMR (400 MHz, DMSO): δ=11.9 (bs, 1H), 8.60-8.61 (m, 1H), 8.15 (bs, 1H), 7.86-7.97 (m, 1H), 7.47-7.50 (m, 1H), 7.47-7.49 (m, 1H), 6.79 (s, 1H), 2.75-2.72 (m, 4H), 2.51-2.69 (m, 4H), 1.76-1.91 (m, 4H); MS (ESI): m/z (%)=382.10 (100%) (M+H)⁺; IR (KBr): ν=3431, 2951, 2187, 1616, 1510, 1197 cm⁻¹.

Example-31

Ethyl ((3-(1,2,3,5,6,7-hexahydro-s-indacen-4-yl)ureido)(oxo)(p-tolyl)-λ⁶-sulfaneylidene)-carbamate

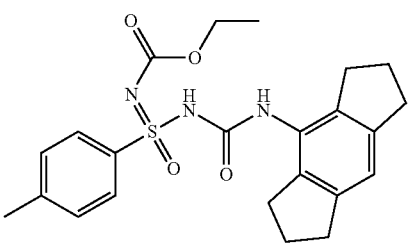 [SMILES: CCOC(=O)N=S(=O)(NC(=O)Nc1c2c(cc3c1CCC3)CCC2)c1ccc(C)cc1]

¹H NMR (400 MHz, DMSO): δ=8.10 (bs, 1H), 7.76-7.78 (m, 2H), 7.31 (d, J=7.2 Hz, 2H), 6.85 (s, 1H), 3.85-3.87 (m, 2H), 2.75-2.78 (m, 4H), 2.61-2.67 (m, 4H), 2.36 (s, 3H), 1.92-1.95 (m, 4H), 1.08 (t, J=7.2 Hz, 3H); MS (ESI): m/z (%)=442.30 (100%) (M+H)⁺; IR (KBr): ν=3348, 2953, 2926, 1656, 1460, 1257 cm⁻¹.

Example-32

N-((3-(1,2,3,5,6,7-hexahydro-s-indacen-4-yl)ureido)(oxo)-(p-tolyl)-λ⁶-sulfaneylidene)-acetamide

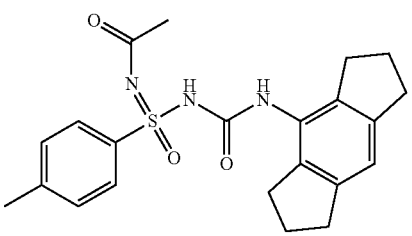 [SMILES: CC(=O)N=S(=O)(NC(=O)Nc1c2c(cc3c1CCC3)CCC2)c1ccc(C)cc1]

¹H NMR (400 MHz, DMSO): δ=11.9 (bs, 1H), 7.80-8.00 (m, 2H), 7.41 (d, J=8 Hz, 2H), 6.89 (s, 1H), 2.71-2.81 (m, 4H), 2.60-2.69 (m, 4H), 2.39 (s, 3H), 1.91-1.98 (m, 7H); MS (ESI): m/z (%)=412.15 (100%) (M+H)⁺; IR (KBr): ν=3265, 2949, 2845, 1720, 1630, 1247 cm⁻¹.

Example-33

N'-carbamoyl-N-((1,2,3,5,6,7-hexahydro-s-indacen-4-yl)carbamoyl)-4-methylbenzenesulfonimidamide

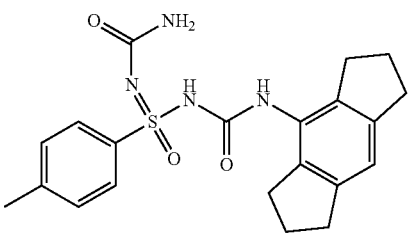 [SMILES: Cc1ccc(S(=O)(=NC(N)=O)NC(=O)Nc2c3c(cc4c2CCC4)CCC3)cc1]

¹H NMR (400 MHz, DMSO): δ=8.60 (bs, 1H), 7.75-7.95 (m, 2H), 7.51 (d, j=8.4 Hz, 2H), 6.90 (s, 1H), 2.77-2.80 (m, 4H), 2.65-2.77 (m, 4H), 2.39 (s, 3H), 1.91-2.00 (m, 4H); MS (ESI): m/z (%)=413.15 (100%) (M+H)⁺.

Example-34

N'-cyano-N-((1,2,3,5,6,7-hexahydro-s-indacen-4-yl)carbamoyl)-3-(2-hydroxypropan-2-yl)benzenesulfonimidamide

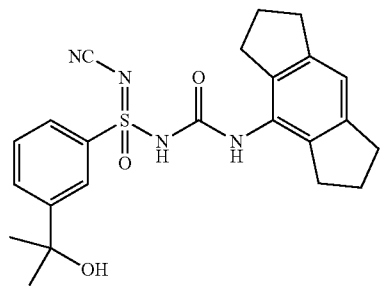 [SMILES: CC(C)(O)c1cccc(S(=O)(=NC#N)NC(=O)Nc2c3c(cc4c2CCC4)CCC3)c1]

$^1$H NMR (400 MHz, DMSO-d$_6$): δ=8.0 (bs, 1H), 7.89 (s, 1H), 7.61-7.55 (m, 2H), 7.41-7.37 (m, 1H), 6.79 (s, 1H), 5.19 (s, 1H), 2.76 (t, J=8.0 Hz, 4H), 2.67 (quin, J=7.2 Hz, 4H), 1.90 (t, J=7.6 Hz, 4H), 1.44 (s, 6H); MS (ESI): m/z (%)=439.15 (100%) (M+H)$^+$; IR (KBr): ν=3400, 3294, 3257, 2976, 2845, 2196, 1593, 1523, 1288, 1224, 1192 cm$^{-1}$.

Example-35

N'-cyano-N-((1,2,3,5,6,7-hexahydro-s-indacen-4-yl)carbamoyl)-4-(3-hydroxyoxetan-3-yl)benzenesulfonimidamide

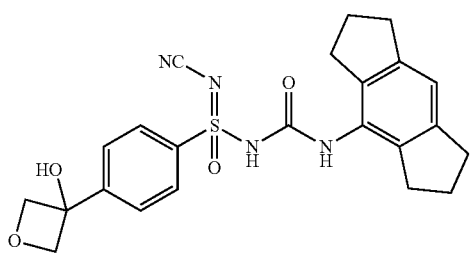 [SMILES: N#CN=S(=O)(NC(=O)Nc1c2c(cc3c1CCC3)CCC2)c1ccc(C2(O)COC2)cc1]

$^1$H NMR (400 MHz, DMSO-d$_6$): δ=8.0 (bs, 1H), 7.79 (d, J=8.8 Hz, 2H), 7.70 (d, J=8.4 Hz, 2H), 6.79 (s, 1H), 6.49 (s, 1H), 4.79 (d, J=6.8 Hz, 2H), 4.71 (d, J=6.0 Hz, 2H), 2.76 (t, J=7.2 Hz, 4H), 2.67 (quin, J=7.2 Hz, 4H), 1.91 (t, J=7.6 Hz, 4H); MS (ESI): m/z (%)=453.25 (100%) (M+H)$^+$.

Example-36

N'-cyano-N-((1,2,3,5,6,7-hexahydro-s-indacen-4-yl)carbamoyl)-4-(prop-1-en-2-yl)furan-2-sulfonimidamide

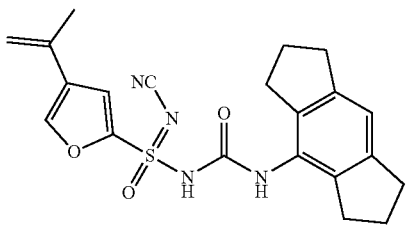 [SMILES: C=C(C)c1coc(S(=O)(=NC#N)NC(=O)Nc2c3c(cc4c2CCC4)CCC3)c1]

$^1$H NMR (400 MHz, DMSO-d$_6$): δ=9.4 (s, 1H), 8.1 (bs, 1H), 7.87 (s, 1H), 7.03 (s, 1H), 6.82 (s, 1H), 5.34 (s, 1H), 4.97 (s, 1H), 2.82-2.73 (m, 4H), 2.68-2.65 (m, 4H), 1.95 (s, 3H), 1.91 (t, J=7.6 Hz, 4H); MS (ESI): m/z (%)=411.13 (100%) (M+H)$^+$, 409.08 (100%) (M−H); IR (KBr): ν=3433, 3255, 2946, 2845, 21963, 1656, 1600, 1531, 1460, 1274 cm$^{-1}$.

Example-37

5-bromo-N'-cyano-N-((1,2,3,5,6,7-hexahydro-s-indacen-4-yl)carbamoyl)thiophene-2-sulfonimidamide

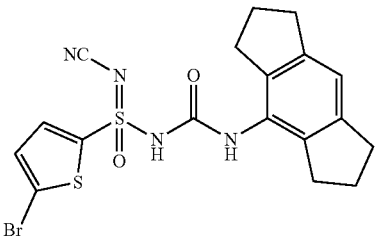 [SMILES: N#CN=S(=O)(NC(=O)Nc1c2c(cc3c1CCC3)CCC2)c1ccc(Br)s1]

$^1$H NMR (400 MHz, DMSO-d$_6$): δ=8.13 (bs, 1H), 7.24 (s, 1H), 7.20 (s, 1H), 6.63 (s, 1H), 2.76 (bs, 4H), 2.68 (q, J=6.4 Hz, 4H), 1.93 (t, J=6.4 Hz, 4H); MS (ESI): m/z (%)=466.10 (100%) (M+H)$^+$, 465.30 (100%) (M−H); IR (KBr): ν=3433, 3244, 2955, 2922, 2202, 2183, 1595, 1533, 1460, 1402, 1276 cm$^{-1}$.

Example-38

N'-cyano-N-((1,2,3,5,6,7-hexahydro-s-indacen-4-yl)carbamoyl)-3-methoxybenzenesulfonimidamide

Example-39

N'-cyano-N-((1,2,3,5,6,7-hexahydro-s-indacen-4-yl)carbamoyl)-4-(2-hydroxypropan-2-yl)furan-2-sulfonimidamide

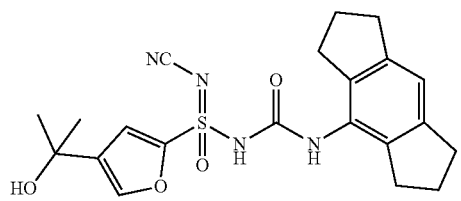 [SMILES: CC(C)(O)c1coc(S(=O)(=NC#N)NC(=O)Nc2c3c(cc4c2CCC4)CCC3)c1]

$^1$H NMR (400 MHz, DMSO-d$_6$): δ=8.10 (bs, 1H), 7.55 (s, 1H), 6.82 (s, 1H), 6.79 (s, 1H), 5.03 (s, 1H), 2.77 (t, J=7.2 Hz, 4H), 2.68 (t, J=7.2 Hz, 4H), 1.94 (qui, J=7.2 Hz, 4H), 1.38 (s, 6H); MS (ESI): m/z (%)=429.20 (100%) (M+H)$^+$, 427.30 (100%) (M−H); IR (KBr): ν=3389, 3138, 2949, 2843, 2191, 1620, 1512, 1274, 1240, 1197, 1118 cm$^{-1}$.

Example-40

N'-cyano-N-((1,2,3,5,6,7-hexahydro-s-indacen-4-yl)carbamoyl)-2,3-dihydrobenzo[b][1,4]dioxine-6-sulfonimidamide

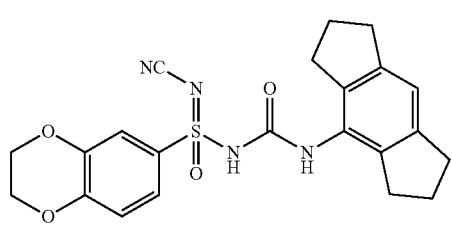 [SMILES: N#CN=S(=O)(NC(=O)Nc1c2c(cc3c1CCC3)CCC2)c1ccc2c(c1)OCCO2]

$^1$H NMR (400 MHz, DMSO-d$_6$): δ=7.96 (bs, 1H), 7.23 (d, J=6.8 Hz, 2H), 6.94 (d, J=9.2 Hz, 1H), 6.80 (s, 1H), 4.28 (s, 4H), 2.76 (t, J=7.2 Hz, 4H), 2.69-2.61 (m, 4H), 1.94 (qui, J=7.2 Hz, 4H); MS (ESI): m/z (%)=439.10 (100%) (M+H)$^+$, 437.10 (100%) (M−H); IR (KBr): ν=3431, 3232, 2928, 2195, 2179, 1595, 1537, 1496, 1458, 1421, 1128, 1151 cm$^{-1}$.

Example-41

N'-cyano-N-((1,2,3,5,6,7-hexahydro-s-indacen-4-yl)carbamoyl)-5-(2-hydroxypropan-2-yl)thiophene-2-sulfonimidamide

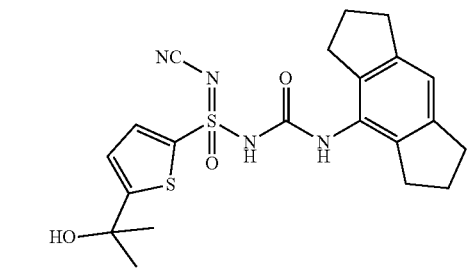 [SMILES: CC(C)(O)c1ccc(S(=O)(=NC#N)NC(=O)Nc2c3c(cc4c2CCC4)CCC3)s1]

$^1$H NMR (400 MHz, DMSO-d$_6$): δ=7.95 (bs, 1H), 7.23 (d, J=4.0 Hz, 1H), 6.82 (d, J=4.0 Hz, 1H), 6.81 (s, 1H), 5.63 (s, 2H), 2.77 (t, J=7.2 Hz, 4H), 2.68-2.65 (m, 4H), 1.94 (qui, J=7.2 Hz, 4H), 1.49 (s, 6H); MS (ESI): m/z (%)=445.10 (100%) (M+H)$^+$, 443.10 (100%) (M−H).

Example-42

N'-cyano-2-fluoro-N-((1,2,3,5,6,7-hexahydro-s-indacen-4-yl)carbamoyl)-5-methylbenzene-sulfonimidamide $^1$H NMR (400 MHz, DMSO-d$_6$): δ=8.06 (bs, 1H), 7.55 (d, J=5.2 Hz, 1H), 7.32-7.30 (m, 1H), 7.16-7.12 (m, 1H), 6.80 (s, 1H), 2.76 (t, J=7.2 Hz, 4H), 2.68-2.64 (m, 4H), 2.31 (s, 3H), 1.94 (qui, J=7.6 Hz, 4H); MS (ESI): m/z (%)=413.13 (100%) (M+H)$^+$; IR (KBr): ν=3433, 3246, 2929, 2845, 2196, 2179, 1595, 1573, 1531, 1492, 1460, 1251 cm$^{-1}$.

---

$^1$H NMR (400 MHz, DMSO-d$_6$): δ=8.26 (bs, 1H), 7.42 (t, J=7.6 Hz, 1H), 7.35 (t, J=8.0 Hz, 1H), 7.28 (t, J=2.0 Hz, 1H), 7.07-7.05 (m, 1H), 6.80 (s, 1H), 3.79 (s, 3H), 2.76 (t, J=7.6 Hz, 4H), 2.68-2.63 (m, 4H), 1.93 (qui, J=6.8 Hz, 4H); MS (ESI): m/z (%)=411.20 (100%) (M+H)$^+$, 409.20 (100%) (M−H); IR (KBr): ν=3423, 3225, 2937, 2848, 2198, 2175, 1597, 1541, 1483, 1460, 1427 cm$^{-1}$.

Example-43

N'-cyano-3-(1,1,1,3,3,3-hexafluoro-2-hydroxypropan-2-yl)-N-((1,2,3,5,6,7-hexahydro-s-indacen-4-yl)carbamoyl)benzenesulfonimidamide

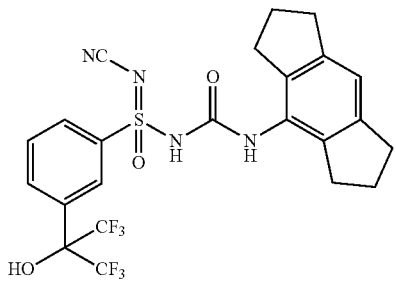 [SMILES: N#CN=S(=O)(NC(=O)Nc1c2c(cc3c1CCC3)CCC2)c1cccc(C(O)(C(F)(F)F)C(F)(F)F)c1]

$^1$H NMR (400 MHz, DMSO-d$_6$): δ=8.95 (s, 1H), 8.14 (S, 1H), 8.04 (s, 1H), 7.92 (d, J=8.0 Hz, 1H), 7.78 (d, J=8.0 Hz, 1H), 7.66 (t, J=7.6 Hz, 1H), 6.79 (s, 1H), 2.75 (t, J=6.8 Hz, 4H), 2.62 (t, J=6.8 Hz, 4H), 1.91 (quin, J=6.8 Hz, 4H); MS (ESI): m/z (%)=547.05 (100%) (M+H)$^+$, 545.10 (100%) (M−H); IR (KBr): ν=3369, 2955, 2847, 2189, 1610, 1510, 1269, 1197 cm$^{-1}$.

Example-44

N'-cyano-3,5-difluoro-N-((1,2,3,5,6,7-hexahydro-s-indacen-4-yl)carbamoyl)benzenesulfonimidamide

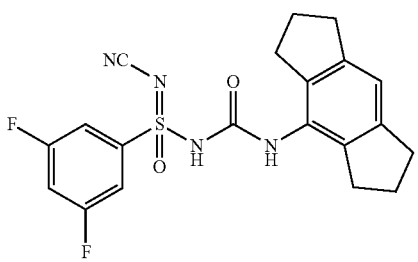 [SMILES: N#CN=S(=O)(NC(=O)Nc1c2c(cc3c1CCC3)CCC2)c1cc(F)cc(F)c1]

$^1$H NMR (400 MHz, DMSO-d$_6$): δ=8.20 (s, 1H), 7.49-7.44 (m, 1H), 7.39-7.34 (m, 2H), 6.82 (S, 1H), 2.72 (t, J=7.2 Hz, 4H), 2.62 (quin, J=7.6 Hz, 4H), 1.94 (t, J=7.2 Hz, 4H); MS (ESI): m/z (%)=417.05 (100%) (M+H)$^+$, 415.05 (100%) (M−H); IR (KBr): ν=3238, 3086, 2956, 2196, 2181, 1597, 1537, 1444, 1278 cm$^{-1}$.

Example 45

N'-cyano-2,4-difluoro-N-((1,2,3,5,6,7-hexahydro-s-indacen-4-yl)carbamoyl)benzenesulfonimidamide

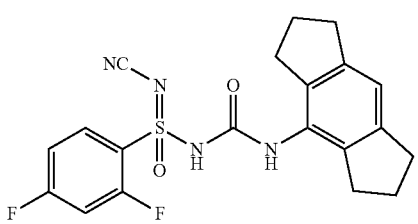 [SMILES: N#CN=S(=O)(NC(=O)Nc1c2c(cc3c1CCC3)CCC2)c1ccc(F)cc1F]

$^1$H NMR (400 MHz, DMSO-d$_6$): δ=8.05 (bs, 1H), 7.84-7.78 (m, 1H), 7.38-7.32 (m, 1H), 7.20-7.15 (m, 1H), 6.80 (S, 1H), 2.76 (t, J=7.2 Hz, 4H), 2.69-2.61 (m, 4H), 1.93 (quin, J=7.2 Hz, 4H); MS (ESI): m/z (%)=416.99 (100%) (M+H)$^+$; IR (KBr): ν=3433, 3255, 2947, 2845, 2195, 1602, 1525, 1487, 1201 cm$^{-1}$.

Example-46

N'-cyano-N-((1,2,3,5,6,7-hexahydro-s-indacen-4-yl)carbamoyl)-3-(trifluoromethoxy)-benzenesulfonimidamide

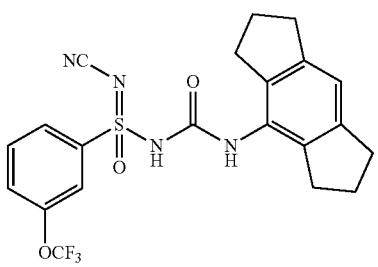 [SMILES: N#CN=S(=O)(NC(=O)Nc1c2c(cc3c1CCC3)CCC2)c1cccc(OC(F)(F)F)c1]

$^1$H NMR (400 MHz, DMSO-d$_6$): δ=8.15 (bs, 1H), 7.78 (d, J=8.0 Hz, 1H), 7.67-7.63 (m, 2H), 7.53 (d, J=8.0 Hz, 1H), 6.80 (S, 1H), 2.76 (t, J=7.2 Hz, 4H), 2.64 (t, J=8.0 Hz, 4H), 1.91 (t, J=4.8 Hz, 4H); MS (ESI): m/z (%)=464.91 (100%) (M)$^+$; IR (KBr): ν=3433, 2953, 2847, 2185, 1608, 1261, 1207 cm$^{-1}$.

Example-47

N'-cyano-N-((2,6-diisopropylphenyl)carbamoyl)-3-(2-hydroxypropan-2-yl)benzenesulfonimidamide

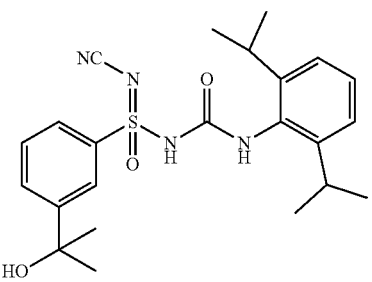 [SMILES: CC(C)c1cccc(C(C)C)c1NC(=O)NS(=O)(=NC#N)c1cccc(C(C)(C)O)c1]

$^1$H NMR (400 MHz, DMSO-d$_6$): δ=7.89 (s, 1H), 7.78 (S, 1H), 7.62 (d, J=7.6 Hz, 1H), 7.56 (d, J=7.6 Hz, 1H), 7.38 (t, J=8.0 Hz, 1H), 7.12 (t, J=7.6 Hz, 1H), 7.01 (d, J=7.6 Hz, 2H), 5.17 (s, 1H), 3.12 (bs, 2H), 1.43 (6, 1H), 1.08 (d, J=6.8 Hz, 12H); MS (ESI): m/z (%)=442.97 (100%) (M+H)$^+$; IR (KBr): ν=3385, 2964, 2868, 2181, 1608, 1475, 1384, 1207, 1128, 844 cm$^{-1}$.

Example-48

N'-cyano-N-((1,2,3,5,6,7-hexahydro-s-indacen-4-yl)carbamoyl)-1-phenylmethanesulfonimidamide

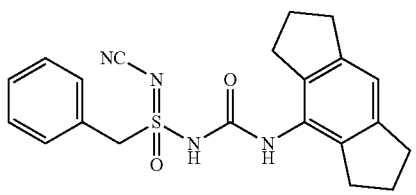 [SMILES: N#CN=S(=O)(Cc1ccccc1)NC(=O)Nc1c2c(cc3c1CCC3)CCC2]

¹H NMR (400 MHz, DMSO-d₆): δ=7.87 (bs, 1H), 7.43-7.30 (m, 5H), 6.84 (S, 1H), 4.66 (d, J=13.2 Hz, 1H), 4.57 (d, J=13.2 Hz, 1H), 2.81-2.72 (m, 8H), 1.99 (quin, J=7.6 Hz, 4H); MS (ESI): m/z (%)=395.15 (100%) (M+H)⁺, 417.14 (20%) (M+Na)⁺; IR (KBr): v=3315, 2945, 2845, 2119, 1604, 1525, 1290, 1234, 1203, 945, 694 cm⁻¹.

Example-49

N-((3-(1,2,3,5,6,7-hexahydro-s-indacen-4-yl)ureido)(3-(2-hydroxypropan-2-yl)phenyl)(oxo)-16-sulfaneylidene)methanesulfonamide

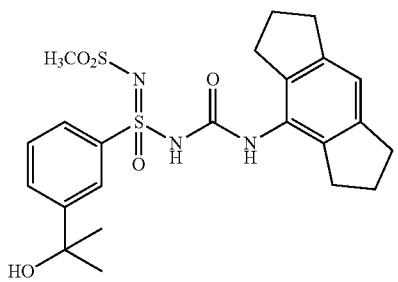

¹H NMR (400 MHz, DMSO-d₆): δ=10.67 (s, 1H), 7.92 (s, 1H), 7.73 (m, 2H), 7.59 (d, J=15.6 Hz, 1H), 7.47-7.43 (m, 4H), 7.26-7.22 (m, 1H), 7.11 (d, J=8.0 Hz, 2H), 3.04-2.97 (m, 2H), 1.04 (s, 12H); MS (ESI): m/z (%)=491.89 (50%) (M+H)⁺, 513.86 (100%) (M+Na), 489.95 (100%) (M−1).

Example-50

N'-cyano-N-((1,2,3,6,7,8-hexahydro-as-indacen-4-yl)carbamoyl)-4-methylbenzenesulfonimidamide

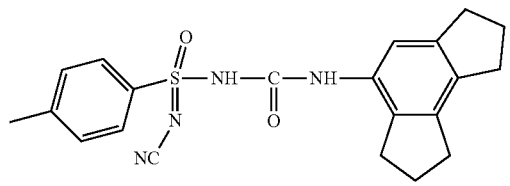 [SMILES: Cc1ccc(S(=O)(=NC#N)NC(=O)Nc2cc3c(c4c2CCC4)CCC3)cc1]

¹H NMR (400 MHz, DMSO-d₆): δ=7.65 (d, J=8.4 Hz, 2H), 7.63 (s, 1H), 7.33 (s, 1H), 7.28 (d, J=8.4 Hz, 2H), 3.09 (m, 4H), 2.67 (m, 4H), 2.35 (s, 3H), 1.97 (m, 4H); MS (ESI): m/z (%)=395.2 (100%) (M+1); IR (KBr): v=3362, 2960, 2847, 2206, 1593, 1519, 1421, 1280, 1182 cm⁻¹.

Example 51

N'-cyano-N-((1,2,3,5,6,7-hexahydro-s-indacen-4-yl)carbamoyl)thiophene-2-sulfonimidamide

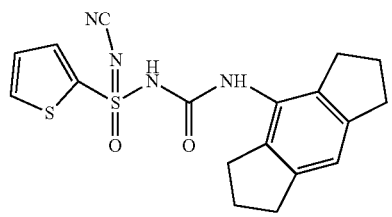 [SMILES: N#CN=S(=O)(NC(=O)Nc1c2c(cc3c1CCC3)CCC2)c1cccs1]

¹H NMR (400 MHz, DMSO-d₆): δ=8.01 (s, 1H), 7.72 (d, J=1.2 Hz, 1H), 7.43 (d, J=2.0 Hz, 1H), 7.06 (d, J=4.8 Hz, 1H), 6.81 (s. 1H), 2.73 (m, 4H), 2.64 (m, 4H), 1.90 (m, 4H); MS (ESI): m/z (%)=387 (M+1).

Example 52

N'-cyano-N-((1,2,3,5,6,7-hexahydro-s-indacen-4-yl)carbamoyl)-3,4-dimethoxybenzene-sulfonimidamide

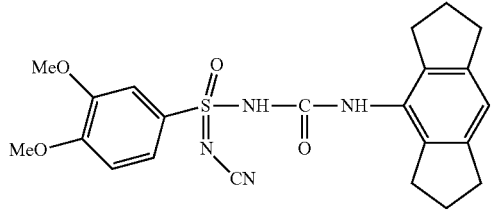 [SMILES: COc1ccc(S(=O)(=NC#N)NC(=O)Nc2c3c(cc4c2CCC4)CCC3)cc1OC]

¹H NMR (400 MHz, DMSO-d₆): δ=7.95 (s, 1H), 7.34 (d, J=2.0 Hz, 1H), 7.29 (d, J=2.0 Hz, 1H), 7.04 (d, J=8.8 Hz, 1H), 6.69 (s, 1H), 3.94 (s, 3H). 3.80 (s, 3H), 2.73 (m, 4H), 2.64 (m, 4H), 2.09 (m, 4H); MS (ESI): m/z (%)=441.2 (100%) (M+1); IR (KBr): v=−3423.76, 2939.6, 2191.21, 1595.18, 1508.38, 1261.49, 941.29 cm⁻¹.

Example 53

N'-cyano-N-((1,2,3,5,6,7-hexahydro-s-indacen-4-yl)carbamoyl)-6-methylpyridine-2-sulfonimidamide

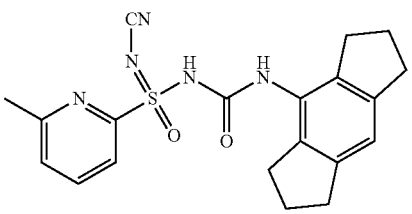 [SMILES: Cc1cccc(S(=O)(=NC#N)NC(=O)Nc2c3c(cc4c2CCC4)CCC3)n1]

¹H NMR (400 MHz, DMSO): δ=8.10 (bs, 1H), 7.85-7.81 (m, 1H), 7.68-7.66 (m, 1H), 7.34-7.36 (m, 1H), 6.79 (s, 1H), 2.75-2.70 (m, 4H), 2.68-2.55 (m, 4H), 2.50 (s, 3H), 1.99-

1.86 (m, 4H); MS (ESI): m/z (%)=396.30 (100%) (M+H)⁺; IR (KBr): v=3367, 2949, 2189, 1732, 1612, 1195 cm⁻¹.

Example 54

N',3-dicyano-N-((1,2,3,5,6,7-hexahydro-s-indacen-4-yl)carbamoyl)benzenesulfonimidamide

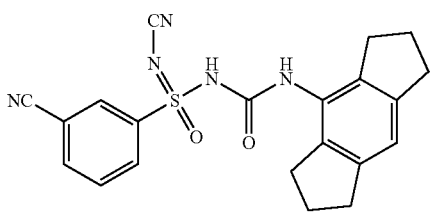 [SMILES: N#CN=S(=O)(NC(=O)Nc1c2c(cc3c1CCC3)CCC2)c1cccc(C#N)c1]

¹H NMR (400 MHz, DMSO): δ=8.20 (bs, 1H), 8.06-7.98 (m, 3H), 7.76-7.72 (m, 1H), 6.81 (s, 1H), 2.76-2.50 (m, 8H), 1.93-1.88 (m, 4H); MS (ESI): m/z (%)=405.95 (100%) (M+H)⁺; IR (KBr): v=3412, 2949, 2191, 1599, 1251, 1205 cm⁻¹.

Example 55

N',4-dicyano-N-((1,2,3,5,6,7-hexahydro-s-indacen-4-yl)carbamoyl)benzenesulfonimidamide

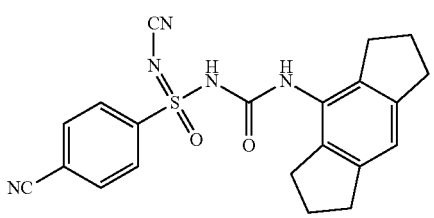 [SMILES: N#CN=S(=O)(NC(=O)Nc1c2c(cc3c1CCC3)CCC2)c1ccc(C#N)cc1]

¹H NMR (400 MHz, DMSO): δ=8.15 (bs, 1H), 8.00-7.97 (m, 2H), 7.89-7.88 (m, 2H), 6.80 (s, 1H), 2.80-2.50 (m, 8H), 1.93-1.19 (m, 4H); MS (ESI): m/z (%)=406.10 (100%) (M+H)⁺; IR (KBr): v=3433, 3246, 2196, 1597, 1246 cm⁻¹.

Example 56

N'-cyano-N-((1,2,3,5,6,7-hexahydro-s-indacen-4-yl)carbamoyl)pyridine-3-sulfonimidamide

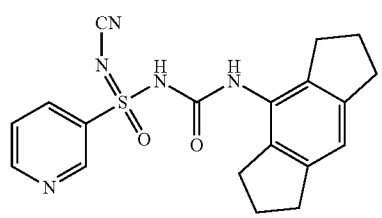 [SMILES: N#CN=S(=O)(NC(=O)Nc1c2c(cc3c1CCC3)CCC2)c1cccnc1]

¹H NMR (400 MHz, DMSO): δ=8.87 (d, J=2 Hz, 1H), 8.67-7.66 (m, 1H), 8.10 (bs, 1H), 8.09-8.07 (m, 1H), 7.56-7.53 (m, 1H), 6.80 (s, 1H), 2.76-2.60 (m, 8H), 1.91-1.87 (m, 4H); MS (ESI): m/z (%)=382.05 (100%) (M+H)⁺; IR (KBr): v=3267, 2951, 2193, 1599, 1257, 1232 cm⁻¹.

Example 57

N'-cyano-N-((1,2,3,5,6,7-hexahydro-s-indacen-4-yl)carbamoyl)pyridine-4-sulfonimidamide

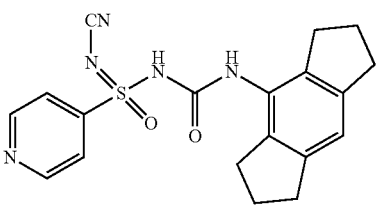 [SMILES: N#CN=S(=O)(NC(=O)Nc1c2c(cc3c1CCC3)CCC2)c1ccncc1]

¹H NMR (400 MHz, DMSO): δ=8.74-8.73 (m, 2H), 8.20 (bs, 1H), 7.66-7.64 (m, 2H), 6.81 (s, 1H), 2.76-2.59 (m, 8H), 1.91-1.87 (m, 4H); MS (ESI): m/z (%)=382.13 (100%) (M+H)⁺; IR (KBr): v=3236, 2951, 2181, 1739, 1599, 1247 cm⁻¹.

Example 58

N'-cyano-3-fluoro-N-((1,2,3,5,6,7-hexahydro-s-indacen-4-yl)carbamoyl)benzenesulfonimidamide

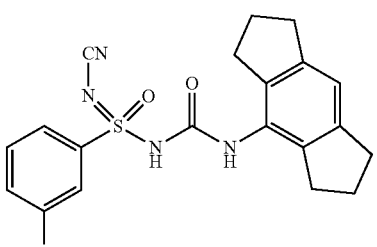

¹H NMR (400 MHz, DMSO-d₆): δ=8.11 (s, 1H), 7.58 (d, J=6.4 Hz, 2H), 7.48 (d, J=8.8 Hz, 1H), 7.37 (d, J=2.8 Hz, 1H), 6.80 (s, 1H), 2.82 (m, 4H), 2.64 (m, 4H), 1.91 (m, 4H); MS (ESI): m/z (%)=397 (100%) (M−1).

Example 59

N'-cyano-N-((1,2,3,5,6,7-hexahydro-s-indacen-4-yl)carbamoyl)quinoline-8-sulfonimidamide

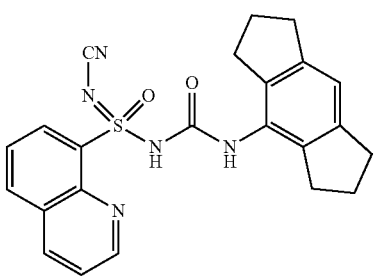 [SMILES: N#CN=S(=O)(NC(=O)Nc1c2c(cc3c1CCC3)CCC2)c1cccc2cccnc12]

¹H NMR (400 MHz, DMSO-d₆): δ=9.02 (s, 1H), 8.64 (d, J=9.2 Hz, 1H), 8.46 (d, J=8.0 Hz, 1H), 8.20 (d, J=7.2 Hz, 1H), 7.78 (m, 1H), 7.72 (d, J=7.6 Hz, 1H), 7.12 (s, 1H), 3.23

(m, 1H), 2.91 (m, 4H), 2.75 (m, 4H), 2.01 (m, 4H); MS (ESI): m/z (%)=432.13 (100%) (M+1).

Example 60

N'-cyano-N-((1,2,3,5,6,7-hexahydro-s-indacen-4-yl)carbamoyl)-4-morpholinobenzene sulfonimidamide

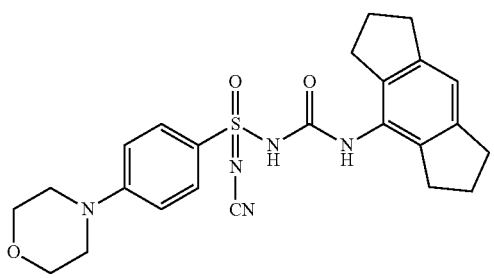 [SMILES: N#CN=S(=O)(NC(=O)Nc1c2c(cc3c1CCC3)CCC2)c1ccc(N2CCOCC2)cc1]

$^1$H NMR (400 MHz, DMSO-d$_6$): δ=7.87 (s, 1H), 7.59 (d, J=9.2 Hz, 2H), 6.97 (d, J=8.8 Hz, 2H), 6.79 (s, 1H), 3.73 (t, J=4.8 Hz, 4H), 3.20 (t, J=4.8 Hz, 4H), 2.85 (m, 4H), 2.65 (m, 4H), 1.91 (m, 4H); MS (ESI): m/z (%)=466.12 (100%) (M+1); IR (KBr): ν=3442, 2949, 2177, 1593, 1504, 1379, 1240, 1190, 927 cm$^{-1}$.

Example 61

N-(3-(N'-cyano-N-((1,2,3,5,6,7-hexahydro-s-indacen-4-yl)carbamoyl)sulfamidimidoyl)phenyl)acetamide

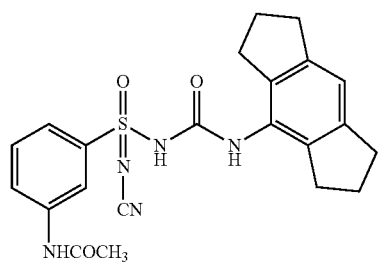

$^1$H NMR (400 MHz, DMSO-d$_6$): δ=10.16 (s, 1H), 7.96 (s, 2H), 7.76 (s, 1H), 7.39 (d, J=2.0 Hz, 2H), 6.79 (s, 1H), 2.85 (m, 4H), 2.55 (m, 4H), 2.05 (s, 3H), 1.85 (m, 4H); MS (ESI): m/z (%)=435.9 (100%) (M−1); IR (KBr): ν=3433, 2918, 2173, 1701, 1599, 1545, 1384, 1215, 1163, 1126, 840 cm$^{-1}$.

Example 62

N'-cyano-N-((1,2,3,5,6,7-hexahydro-s-indacen-4-yl)carbamoyl)-3-morpholinobenzene sulfonimidamide

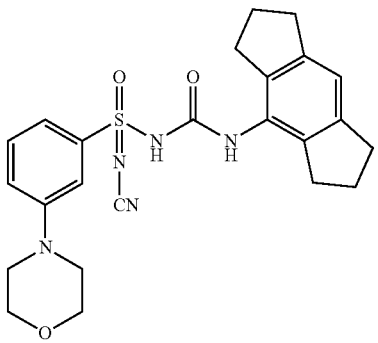 [SMILES: N#CN=S(=O)(NC(=O)Nc1c2c(cc3c1CCC3)CCC2)c1cccc(N2CCOCC2)c1]

$^1$H NMR (400 MHz, DMSO-d$_6$): δ=8.0 (s, 1H), 7.31 (d, J=8.0 Hz, 2H), 7.20 (d, J=8.0 Hz, 2H), 7.07 (d, J=1.60 Hz, 1H), 6.80 (s, 1H), 3.75 (t, J=4.8 Hz, 4H), 3.12 (t, J=4.8 Hz, 4H), 2.74 (m, 4H), 2.71 (m, 4H), 1.95 (m, 4H); MS (ESI): m/z (%)=465.98 (100%) (M+1); IR (KBr): ν=3433, 3225, 2955, 2195, 1595, 1539, 1485, 1379, 1280, 1120, 937 cm$^{-1}$.

Example 63

N'-cyano-4-fluoro-N-((1,2,3,5,6,7-hexahydro-s-indacen-4-yl)carbamoyl)-3-(2-hydroxypropan-2-yl)benzenesulfonimidamide

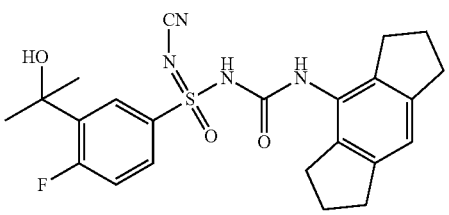 [SMILES: CC(C)(O)c1cc(S(=O)(=NC#N)NC(=O)Nc2c3c(cc4c2CCC4)CCC3)ccc1F]

$^1$H NMR (400 MHz, DMSO): δ=8.13 (dd, J=2.4 Hz, J=7.6 Hz, 1H), 8.00 (bs, 1H), 7.68-7.64 (m, 1H), 7.24-7.19 (m, 2H), 6.79 (s, 1H), 2.76-2.60 (m, 8H), 1.95-1.85 (m, 4H), 1.50 (s, 3H), 1.48 (s, 3H); MS (ESI): m/z (%)=456.88 (100%) (M+H)$^+$; IR (KBr): ν=3369, 2953, 2185, 1614, 1215 cm$^{-1}$.

Example 64

N'-cyano-2-fluoro-N-((1,2,3,5,6,7-hexahydro-s-indacen-4-yl)carbamoyl)-5-(2-hydroxypropan-2-yl)benzenesulfonimidamide

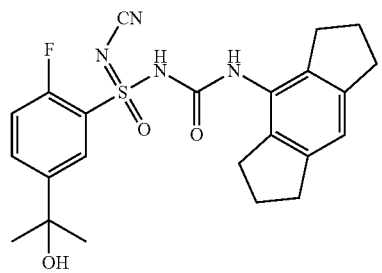 [SMILES: CC(C)(O)c1ccc(F)c(S(=O)(=NC#N)NC(=O)Nc2c3c(cc4c2CCC4)CCC3)c1]

$^1$H NMR (400 MHz, DMSO): δ=8.10 (bs, 1H), 7.88 (dd, J=2.4 Hz, J=7.2 Hz, 1H), 7.56-7.55 (m, 1H), 7.19-7.15 (m, 1H), 6.80 (s, 1H), 5.22 (s, 1H), 2.76-2.61 (m, 8H), 1.99-1.87 (m, 4H), 1.42 (s, 6H); MS (ESI): m/z (%)=456.90 (100%) (M+H)$^+$; IR (KBr): ν=3412, 2949, 2196, 1595, 1195 cm$^{-1}$.

Example 65

N'-cyano-N-((1,2,3,5,6,7-hexahydro-s-indacen-4-yl)carbamoyl)-5-(2-hydroxypropan-2-yl)pyridine-3-sulfonimidamide

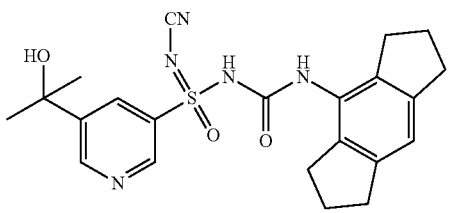 [SMILES: CC(C)(O)c1cncc(S(=O)(=NC#N)NC(=O)Nc2c3c(cc4c2CCC4)CCC3)c1]

$^1$H NMR (400 MHz, DMSO): δ=8.75-8.72 (m, 2H), 8.22-8.14 (m, 2H), 6.80 (s, 1H), 5.43 (s, 1H), 2.90-2.60 (m, 8H), 1.99-1.76 (m, 4H), 1.48 (s, 3H), 1.47 (s, 3H); MS (ESI): m/z (%)=439.83 (100%) (M+H)$^+$.

Example 66

N'-cyano-1-(4-cyanophenyl)-N-((1,2,3,5,6,7-hexahydro-s-indacen-4-yl)carbamoyl)-methanesulfonimidamide

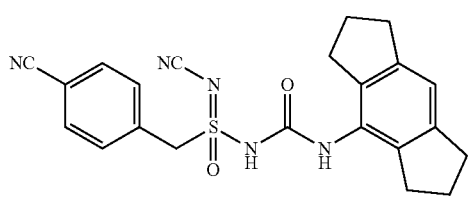 [SMILES: N#CN=S(=O)(Cc1ccc(C#N)cc1)NC(=O)Nc1c2c(cc3c1CCC3)CCC2]

$^1$H NMR (400 MHz, DMSO-d$_6$): δ=7.94 (bs, 1H), 7.82 (d, J=8.4 Hz, 2H), 7.54 (d, J=8.0 Hz, 2H), 6.84 (S, 1H), 4.78 (d, J=13.2 Hz, 1H), 4.68 (d, J=12.8 Hz, 1H), 2.79 (t, J=7.2 Hz, 4H), 2.73 (t, J=7.2 Hz, 4H), 1.97 (quin, J=7.2 Hz, 4H); MS (ESI): m/z (%)=420.17 (100%) (M+H)$^+$, 442.15 (20%) (M+Na)$^+$; IR (KBr): ν=3290, 2951, 2850, 2229, 2189, 1720, 1602, 1529, 1460, 1286, 1228, 1161 cm$^{-1}$.

Example 67

1-(4-cyanophenyl)-N-((1,2,3,5,6,7-hexahydro-s-indacen-4-yl)carbamoyl)methanesulfonimidamide

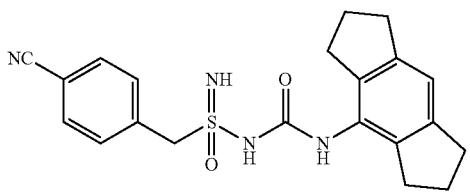 [SMILES: N#Cc1ccc(CS(=N)(=O)NC(=O)Nc2c3c(cc4c2CCC4)CCC3)cc1]

$^1$H NMR (400 MHz, DMSO-d$_6$): δ=8.2 (bs, 1H), 7.78 (d, J=8.0 Hz, 2H), 7.58 (d, J=7.6 Hz, 2H), 7.06 (S, 2H), 6.89 (S, 1H), 4.89 (d, J=13.2 Hz, 1H), 4.75 (d, J=13.2 Hz, 1H), 2.80 (t, J=7.2 Hz, 4H), 2.67 (t, J=7.2 Hz, 4H), 1.96 (t, J=7.2 Hz, 4H); MS (ESI): m/z (%)=395.15 (50%) (M+H)$^+$, 393.04 (100%) (M−H)$^+$; IR (KBr): ν=3275, 3176, 2949, 2843, 2231, 1618, 1531, 1460, 1288, 1246, 1151, 829 cm$^{-1}$.

Example 68

N'-cyano-3-(2-hydroxypropan-2-yl)-N-((3-oxo-1,2,3,5,6,7-hexahydro-s-indacen-4-yl)carba-moyl)-benzenesulfonimidamide

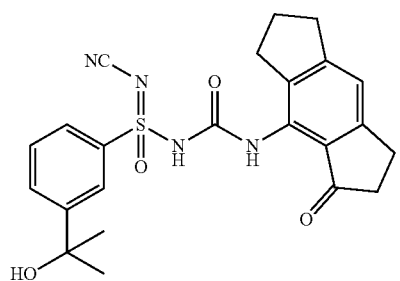 [SMILES: CC(C)(O)c1cccc(S(=O)(=NC#N)NC(=O)Nc2c3c(cc4c2C(=O)CC4)CCC3)c1]

$^1$H NMR (400 MHz, DMSO-d$_6$): δ=8.89 (s, 1H), 7.92 (S, 1H), 7.60 (q, J=7.6 Hz, 2H), 7.41 (t, J=7.6 Hz, 1H), 7.00 (s, 1H), 5.21 (s, 1H), 2.82 (t, J=4.4 Hz, 2H), 2.82 (t, J=7.6 Hz, 2H), 2.77-2.67 (m, 4H), 1.85 (t, J=6.0 Hz, 2H), 1.43 (s, 6H); MS (ESI): m/z (%)=453.35 (100%) (M+H)$^+$, 475.35 (50%) (M+Na)$^+$; IR (KBr): ν=3421, 2964, 2926, 2181, 1672, 1651, 1614, 1508, 1460, 1419, 1251, 1190 cm$^{-1}$.

Biological Activity:
In-Vitro Assays:
THP1 (Tamm-Horsfall Protein 1) monocytes were differentiated with PMA (Phorbol 12-myristate 13-acetate) (100 ng/ml) and incubated at 37° C. for 20 h in presence of 5% CO$_2$. 2×10$^5$ differentiated cells were plated per well of 96 well tissue culture plates. The cells were primed using 500 ng/ml Lipopolysaccharide and incubating for 4 hrs under the same condition. The cells were then treated with various concentrations of the compounds for 30 min followed by treatment with 5 mM ATP for 1 hr. The supernatants were collected and analysed by IL-1b (Mabtech Cat #3415-1H-

20) or TNF-a (Mabtech; Cat #3510-1H-20) detection kit. The data were analyzed using GraphPad Prism V7.0. Dose Response Curve (DRC) was constructed to determine the $IC_{50}$ value by fitting percentage cell survival data to the GraphPad Prism using nonlinear regression analysis. The in vitro IL-1β inhibitory activity ($IC_{50}$) for representative compounds is listed in Table 1:

TABLE 1

| Compound | $IC_{50}$ (nM) |
| --- | --- |
| Example 1 | 6.6 |
| Example 17 | 12 |
| Example 18 | 15 |
| Example 19 | 23 |
| Example 21 | 62 |
| Example 22 | 13 |
| Example 24 | 34 |
| Example 25 | 5 |
| Example 26 | 23 |
| Example 27 | 27 |
| Example 29 | 32 |
| Example 30 | 28 |
| Example 34 | 3 |
| Example 35 | 13 |
| Example 36 | 32 |
| Example 37 | 5.6 |
| Example 38 | 17 |
| Example 39 | 3.3 |
| Example 40 | 13 |
| Example 41 | 4.8 |
| Example 42 | 2.4 |
| Example 43 | 27 |
| Example 44 | 63 |
| Example 45 | 23 |
| Example 46 | — |
| Example 48 | 3.5 |
| Example 51 | 19 |
| Example 52 | 4.4 |
| Example 53 | 45 |
| Example 54 | 12 |
| Example 55 | 27 |
| Example 56 | 43 |
| Example 58 | 38 |
| Example 63 | 7.8 |
| Example 64 | 7.7 |
| Example 65 | 1.26 |
| Example 66 | 4 |

In Vivo Efficacy Studies:

Demonstration of in vivo efficacy of test compounds in rats mice, oral routes of administration.

Animals

All the animal experiments were carried out in female rats and mice, bred in-house. Animals were housed in groups of 6 animals per cage, for a week, in order to habituate them to vivarium conditions (25±4° C., 60-65% relative humidity, 12:12 h light:dark cycle, with lights on at 7.30 am). All the animal experiments were carried out according to the internationally valid guidelines following approval by the 'Zydus Research Center animal ethical committee'.

In-Vivo LPS and ATP Induced IL-1β Assay:

Female C57 mice (6-8 weeks) received intraperitoneal injection of 50 μg/mouse of lipopolysaccharide (LPS) in PBS. Animals were treated immediately with the test compounds or the vehicle. After 2 h of LPS injection, animals were administered with ATP at 12.5 mg/mouse dissolved in PBS via intraperitoneal route. After 30 minutes of ATP injection, serum was collected for IL-1β estimation by ELISA.

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as a medicament for the inhibition of NLRP3 activity and suitable for humans and other warm blooded animals, and may be administered either by oral, topical or parenteral administration. Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (I) are NLRP3 inhibitors and are useful in the treatment of disease states mediated by NLRP3, preferably diseases or conditions in which interleukin 1 β activity in which interleukin 1β activity and interleukin-18 (IL-18) are implicated and related disorders.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention, formula (I), may be used alone or in any combination with one or more other therapeutic agents which a skilled medical practitioner can easily identify. Such other therapeutic agent may be selected depending on the type of disease being treated, the severity, other medications being taken by the patients etc. Thus for example, for treatment of rheumatoid arthritis, one or more DMARDs may be used in combination with the compounds of the present invention.

In one of the embodiments compound of formula (I) of the present invention may be used in combination with one or more suitable pharmaceutically active agents selected from following therapeutic agents in any combination. Inhibitors of interleukin-1β (e.g. rilonacept, canakinumab, and anakinra); immune-suppressants (e.g., Methotrexate, mercaptopurine, cyclophosphamide), metabolic disorders drugs, glucocorticoids, non-steroidal anti-inflammatory drugs, Cox-2 specific inhibitors, TNF-α binding proteins (eg., Infliximab, etanercept), interferon-13, interferon, interleukin-2, antihistamines, beta-agonist, BTK inhibitors, anti-cholinergics, anti-cancer agents or their suitable pharmaceutically acceptable salts. Further examples for use in combination with Non-Alcoholic Steato-Hepatitis (NASH) and fibrosis drugs, anticancer antibiotics, hormones, Aromatase inhibitors, antibodies, cytokines, vaccines, drug conjugates, inhibitors of mitogen-activated protein kinase signaling (ex: BAY 43-9006), Syk inhibitors, mTOR inhibitors, antibodies (Rituxan), and BCR/ABL antagonist.

What is claimed is:

1. A compound having the structure of general formula (I)

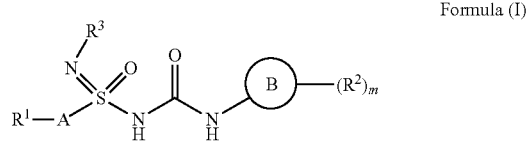

Formula (I)

wherein

'A' is selected from unsubstituted or substituted ($C_1$-$C_6$) alkyl, ($C_2$-$C_6$)alkenyl, ($C_3$-$C_6$)cycloalkyl, aryl, heteroaryl and heterocyclyl groups having optionally one or more than one heteroatom;

'B' is the following ring system

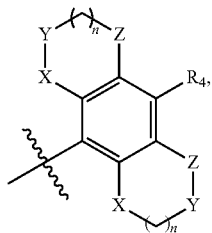

wherein X, Y, Z at each occurrence is independently selected from C, N, S, $SO_2$, and O, which may be optionally substituted;

n=0-3;

$R^1$ at each occurrence independently represents hydrogen, halogen, haloalkyl, cyano, optionally substituted groups selected from ($C_1$-$C_6$)alkyl, ($C_2$-$C_6$)alkenyl, ($C_1$-$C_6$)alkoxy, ($C_3$-$C_6$)cycloalkyl, aryl, heteroaryl, heterocyclyl, benzyl, mercapto alkyl, sulfur and its oxidized forms;

when A represents a ring, $R^1$ may additionally represent thiol, sulfur and its oxidized forms, $C_1$-$C_6$(thio-alkoxy), bridged or spiro ring system having optionally one or more than one heteroatom;

$R^2$ at each occurrence independently represents hydrogen, halide, cyano, optionally substituted groups selected from ($C_1$-$C_6$)alkyl, ($C_2$-$C_6$)alkenyl, ($C_1$-$C_6$)alkoxy ($C_3$-$C_6$)cycloalkyl, benzyl, aryl, heteroaryl, heterocyclyl, thiol, thioalkyl, thio-alkoxy sulfur and its oxidized forms, bridged or spiro ring system having optionally one or more than one heteroatom;

$R^3$ at each occurrence independently represents hydrogen, hydroxyl, halogen, nitro, cyano, optionally substituted groups selected from ($C_1$-$C_{10}$)alkyl, ($C_1$-$C_{10}$)alkoxy, ($C_3$-$C_{10}$)cycloalkyl, ($C_2$-$C_{10}$)alkenyl, ($C_2$-$C_{10}$)alkynyl, $SO_2$($C_1$-$C_6$)alkyl, benzyl, aryl, heteroaryl, heterocyclyl, thiol, thioalkyl, thio-alkoxy, sulfur and its oxidized forms, or $R^3$ and A together with the atom to which they are attached may form an optionally substituted 5 to 7 membered heterocyclic ring system having optionally one or more than one heteroatom; 'm' represents an integer from 1-5;

$R_4$ at each occurrence is independently selected from hydrogen, halogen, cyano, amide, sulphonamide, acyl, hydroxyl, optionally substituted groups selected from ($C_1$-$C_6$)alkyl, ($C_1$-$C_6$)haloalkyl, ($C_3$-$C_6$)cycloalkyl, and ($C_1$-$C_6$)alkoxy;

wherein the substitutions on any of the optionally substituted groups above are independently selected from hydrogen, hydroxy, cyano, halo, haloalkyl, haloalkyloxy, alkylthio ($C_1$-$C_6$)alkyl, ($C_2$-$C_6$)alkenyl, ($C_2$-$C_6$) alkynyl, ($C_3$-$C_{10}$)cycloalkyl, $C_1$-$C_6$alkoxy, —$COR_{10}$, —$CSR_{10}$, $C(O)OR_{10}$, $C(O)$—$R_{10}$, —$C(O)$—$NR_{11}R_{12}$, —$C(S)$—$NR_{11}R_{12}$, —$SO_2R_{10}$ group, wherein $R_{10}$ is independently selected from hydrogen, optionally substituted group selected from ($C_1$-$C_6$)alkyl, ($C_2$-$C_6$)alkenyl, ($C_2$-$C_6$)alkynyl, ($C_3$-$C_7$)cycloalkyl, aryl, heteroaryl, and heterocyclyl group; each of $R_{11}$ and $R_{12}$ are independently selected from hydrogen, optionally substituted group selected from ($C_1$-$C_6$)alkyl, ($C_1$-$C_6$) alkoxy, aryl and benzyl group.

2. The compound as claimed in claim 1, wherein $R_4$ at each occurrence is independently selected from hydrogen, halogen, ($C_1$-$C_6$)alkyl, and ($C_1$-$C_6$)alkoxy groups.

3. A compound as claimed in claim 1 selected from the group consisting of:

N'-cyano-N-((1,2,3,5,6,7-hexahydro-s-indacen-4-yl)carbamoyl)-4-methylbenzene sulfonimidamide;

N'-cyano-N-((2,6-diisopropylphenyl)carbamoyl)-4-methylbenzenesulfonimidamide;

N-((1,2,3,5,6,7-hexahydro-s-indacen-4-yl)carbamoyl)-4-methylbenzenesulfonimidamide;

N-((2,6-diisopropylphenyl)carbamoyl)-4-methylbenzenesulfonimidamide;

N-((2,6-diisopropylphenyl)carbamoyl)-4-methyl-N'-(2,2,2-trifluoroethyl)benzenesulfonimidamide;

N-((1,2,3,5,6,7-hexahydro-s-indacen-4-yl)carbamoyl)-4-methyl-N'-(2,2,2-trifluoroethyl)-benzenesulfonimidamide;

N-((2,6-diisopropylphenyl)carbamoyl)-N'-methoxy-4-methylbenzenesulfonimidamide;

N-((1,2,3,5,6,7-hexahydro-s-indacen-4-yl)carbamoyl)-N'-isopropyl-4-methylbenzenesulfonimidamide;

N-((2,6-diisopropylphenyl)carbamoyl)-N'-isopropyl-4-methylbenzenesulfonimidamide;

N-((1,2,3,5,6,7-hexahydro-s-indacen-4-yl)carbamoyl)-N'-methoxy-4-methylbenzenesulfo-nimidamide;

N-((1,2,3,5,6,7-hexahydro-s-indacen-4-yl)carbamoyl)-N',4-dimethylbenzenesulfonimidamide;

N-((1,2,3,5,6,7-hexahydro-s-indacen-4-yl)carbamoyl)-4-methyl-N'-(1H-pyrazol-5-yl)benzenesulfonimidamide;

N'-(4-fluorophenyl)-N-((1,2,3,5,6,7-hexahydro-s-indacen-4-yl)carbamoyl)-4-methylbenzenesulfonimidamide;

N-((1,2,3,5,6,7-hexahydro-s-indacen-4-yl)carbamoyl)-4-methyl-N'-(pyridin-2-yl)benzenesulfonimidamide;

4-acetyl-N'-cyano-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)-4-(2-hydroxypropan-2-yl)benzenesulfonimidamide;

N'-cyano-N-((1,2,3,5,6,7-hexahydro-s-indacen-4-yl)carbamoyl)-3-nitrobenzenesulfonimidamide;

N'-cyano-N-((1,2,3,5,6,7-hexahydro-s-indacen-4-yl)carbamoyl)-4-methoxybenzenesulfonimidamide;

N'-cyano-N-((2,6-diisopropylphenyl)carbamoyl)-4-methoxybenzenesulfonimidamide;

N'-cyano-4-fluoro-N-((1,2,3,5,6,7-hexahydro-s-indacen-4-yl)carbamoyl)benzenesulfonimidamide;

N'-cyano-N-((1,2,3,5,6,7-hexahydro-s-indacen-4-yl)carbamoyl)benzenesulfonimidamide;

N-((3-(1,2,3,5,6,7-hexahydro-s-indacen-4-yl)ureido)(oxo)(p-tolyl)-1 6-sulfanylidene)-methanesulfonamide;

N'-cyano-N-((1,2,3,5,6,7-hexahydro-s-indacen-4-yl)carbamoyl)-6-methoxypyridine-3-sulfonimidamide;

N'-cyano-3-fluoro-N-((1,2,3,5,6,7-hexahydro-s-indacen-4-yl)carbamoyl)-4-methylbenzenesulfonimidamide;

4-chloro-N'-cyano-N-((1,2,3,5,6,7-hexahydro-s-indacen-4-yl)carbamoyl)benzenesulfonimidamide;

4-bromo-N'-cyano-N-((1,2,3,5,6,7-hexahydro-s-indacen-4-yl)carbamoyl)benzenesulfonimidamide;

4-(benzyloxy)-N'-cyano-N-((1,2,3,5,6,7-hexahydro-s-indacen-4-yl)carbamoyl)benzene-sulfonimidamide;

N'-cyano-N-((1,2,3,5,6,7-hexahydro-s-indacen-4-yl)carbamoyl)-4-(trifluoromethyl)-benzenesulfonimidamide;

N'-cyano-N-((1,2,3,5,6,7-hexahydro-s-indacen-4-yl)carbamoyl)pyridine-2-sulfonimidamide;

ethyl ((3-(1,2,3,5,6,7-hexahydro-s-indacen-4-yl)ureido)(oxo)(p-tolyl)-λ⁶-sulfanylidene)-carbamate;
N-((3-(1,2,3,5,6,7-hexahydro-s-indacen-4-yl)ureido)(oxo)-(p-tolyl)-λ⁶-sulfanylidene)-acetamide;
N'-carbamoyl-N-((1,2,3,5,6,7-hexahydro-s-indacen-4-yl)carbamoyl)-4-methylbenzenesulfonimidamide;
N'-cyano-N-((1,2,3,5,6,7-hexahydro-s-indacen-4-yl)carbamoyl)-3-(2-hydroxypropan-2-yl)benzenesulfonimidamide;
N'-cyano-N-((1,2,3,5,6,7-hexahydro-s-indacen-4-yl)carbamoyl)-4-(3-hydroxyoxetan-3-yl)benzenesulfonimidamide;
N'-cyano-N-((1,2,3,5,6,7-hexahydro-s-indacen-4-yl)carbamoyl)-4-(prop-1-en-2-yl)furan-2-sulfonimidamide;
5-bromo-N'-cyano-N-((1,2,3,5,6,7-hexahydro-s-indacen-4-yl)carbamoyl)thiophene-2-sulfonimidamide;
N'-cyano-N-((1,2,3,5,6,7-hexahydro-s-indacen-4-yl)carbamoyl)-3-methoxybenzenesulfonimidamide;
N'-cyano-N-((1,2,3,5,6,7-hexahydro-s-indacen-4-yl)carbamoyl)-4-(2-hydroxypropan-2-yl)furan-2-sulfonimidamide
N'-cyano-N-((1,2,3,5,6,7-hexahydro-s-indacen-4-yl)carbamoyl)-2,3-dihydrobenzo[b][1,4] dioxine-6-sulfonimidamide;
N'-cyano-N-((1,2,3,5,6,7-hexahydro-s-indacen-4-yl)carbamoyl)-5-(2-hydroxypropan-2-yl)thiophene-2-sulfonimidamide;
N'-cyano-2-fluoro-N-((1,2,3,5,6,7-hexahydro-s-indacen-4-yl)carbamoyl)-5-methylbenzenesulfonimidamide;
N'-cyano-3-(1,1,1,3,3,3-hexafluoro-2-hydroxypropan-2-yl)-N-((1,2,3,5,6,7-hexahydro-s-indacen-4-yl)carbamoyl)benzenesulfonimidamide
N'-cyano-3,5-difluoro-N-((1,2,3,5,6,7-hexahydro-s-indacen-4-yl)carbamoyl)benzenesulfonimidamide;
N'-cyano-2,4-difluoro-N-((1,2,3,5,6,7-hexahydro-s-indacen-4-yl)carbamoyl)benzenesulfonimidamide;
N'-cyano-N-((1,2,3,5,6,7-hexahydro-s-indacen-4-yl)carbamoyl)-3-(trifluoromethoxy)-benzenesulfonimidamide;
N'-cyano-N-((2,6-diisopropylphenyl)carbamoyl)-3-(2-hydroxypropan-2-yl)benzenesulfonimidamide;
N'-cyano-N-((1,2,3,5,6,7-hexahydro-s-indacen-4-yl)carbamoyl)-1-phenylmethanesulfonimidamide;
N-((3-(1,2,3,5,6,7-hexahydro-s-indacen-4-yl)ureido)(3-(2-hydroxypropan-2-yl)phenyl)(oxo)-16-sulfaneylidene)methanesulfonamide;
N'-cyano-N-((1,2,3,6,7,8-hexahydro-as-indacen-4-yl)carbamoyl)-4-methylbenzenesulfonimidamide;
N'-cyano-N-((1,2,3,5,6,7-hexahydro-s-indacen-4-yl)carbamoyl)thiophene-2-sulfonimidamide;
N'-cyano-N-((1,2,3,5,6,7-hexahydro-s-indacen-4-yl)carbamoyl)-3,4-dimethoxybenzene-sulfonimidamide;
N'-cyano-N-((1,2,3,5,6,7-hexahydro-s-indacen-4-yl)carbamoyl)-6-methylpyridine-2-sulfonimidamide;
N',3-dicyano-N-((1,2,3,5,6,7-hexahydro-s-indacen-4-yl)carbamoyl)benzenesulfonimidamide;
N',4-dicyano-N-((1,2,3,5,6,7-hexahydro-s-indacen-4-yl)carbamoyl)benzenesulfonimidamide;
N'-cyano-N-((1,2,3,5,6,7-hexahydro-s-indacen-4-yl)carbamoyl)pyridine-4-sulfonimidamide;
N'-cyano-3-fluoro-N-((1,2,3,5,6,7-hexahydro-s-indacen-4-yl)carbamoyl)benzene sulfonimidamide;
N'-cyano-N-((1,2,3,5,6,7-hexahydro-s-indacen-4-yl)carbamoyl)quinoline-8-sulfonimidamide;
N'-cyano-N-((1,2,3,5,6,7-hexahydro-s-indacen-4-yl)carbamoyl)-4-morpholinobenzene sulfonimidamide;
N-(3-(N'-cyano-N-((1,2,3,5,6,7-hexahydro-s-indacen-4-yl)carbamoyl)sulfamidimidoyl)phenyl) acetamide;
N'-cyano-N-((1,2,3,5,6,7-hexahydro-s-indacen-4-yl)carbamoyl)-3-morpholinobenzene sulfonimidamide;
N'-cyano-4-fluoro-N-((1,2,3,5,6,7-hexahydro-s-indacen-4-yl)carbamoyl)-3-(2-hydroxypropan-2-yl)benzenesulfonimidamide;
N'-cyano-2-fluoro-N-((1,2,3,5,6,7-hexahydro-s-indacen-4-yl)carbamoyl)-5-(2-hydroxypropan-2-yl)benzenesulfonimidamide;
N'-cyano-N-((1,2,3,5,6,7-hexahydro-s-indacen-4-yl)carbamoyl)-5-(2-hydroxypropan-2-yl)pyridine-3-sulfonimidamide;
N'-cyano-1-(4-cyanophenyl)-N-((1,2,3,5,6,7-s-indacen-4-yl)carbamoyl)-methanesulfonimidamide;
1-(4-cyanophenyl)-N-((1,2,3,5,6,7-hexahydro-s-indacen-4-yl)carbamoyl)methanesulfonimidamide; and
N'-cyano-3-(2-hydroxypropan-2-yl)-N-((3-oxo-1,2,3,5,6,7-hexahydro-s-indacen-4-yl)carba-moyl)-benzenesulfonimidamide.

4. A pharmaceutical composition comprising a therapeutically effective amount of a compound of Formula (I) as claimed in claim 1 and optionally one or more pharmaceutically acceptable carriers, diluents or excipients.

5. The pharmaceutical composition as claimed in claim 4 in combination with one or more suitable pharmaceutically active agents selected from inhibitors of interleukin-1β; immune-suppressants; metabolic disorders drugs, glucocorticoids, non-steroidal anti-inflammatory drugs, COX-2 specific inhibitors, TNF-α binding proteins, interferon-13, interferon, interleukin-2, antihistamines, beta-agonists, BTK inhibitors, anticholinergics, anti-cancer agents or their suitable pharmaceutically acceptable salts, Non-Alcoholic Steato-Hepatitis (NASH) and fibrosis drugs, antibiotics, hormones, aromatase inhibitors, inhibitors of mitogen-activated protein kinase signaling, Syk inhibitors, mTOR inhibitors, and BCR/ABL antagonists.

6. A method of administering the composition of claim 4 for treating diseases or conditions in which interleukin 1 activity and interleukin-18 (IL-18) are implicated selected from lymphoma, inflammatory bowel diseases (IBD), autoimmune diseases, heteroimmune diseases, inflammatory diseases, cancer, and neurodegenerative diseases.

7. A method of administering the composition of claim 4 for treating diseases or conditions in which interleukin 1 activity and interleukin-18 (IL-18) are implicated selected from inflammation, Cryopyrin-associated periodic syndromes (CAPS), gouty arthritis, type 2 diabetes, atherosclerosis, and liver fibrosis.

* * * * *